US006492389B1

(12) United States Patent
Huang et al.

(10) Patent No.: US 6,492,389 B1
(45) Date of Patent: Dec. 10, 2002

(54) SMALL MOLECULE INHIBITORS OF BCL-2 PROTEINS

(75) Inventors: Ziwei Huang, Philadelphia, PA (US); Dongxiang Liu, Philadelphia, PA (US); Xiaobing Han, Voorhees, NJ (US); Zhijia Zhang, Cherry Hill, NJ (US); Jialun Wang, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/357,229

(22) Filed: Jul. 20, 1999

Related U.S. Application Data

(60) Provisional application No. 60/128,100, filed on Apr. 7, 1999, and provisional application No. 60/093,561, filed on Jul. 21, 1998.

(51) Int. Cl.[7] .............................................. A61K 31/47
(52) U.S. Cl. ....................... 514/311; 514/299; 514/312; 514/313; 514/434; 514/454; 514/456
(58) Field of Search .................. 514/299, 311, 514/312, 313, 434, 456

(56) References Cited

U.S. PATENT DOCUMENTS 5,028,606 A  7/1991  Venet et al. ................. 514/249

OTHER PUBLICATIONS

Castle et al., *Am. J. Pathol.*, 143(6):1543–1550 (Dec. 1993).
Ellis et al., *Annu. Rev. Cell Biol.*, 7:663–698 (1991).
Garchon et al., *Eur. J. Immunol.*, 24:380–384 (1994).
Haldar et al., *Cancer Res.*, 56:1235–5 (1996).
Hanada et al., *Cancer Res.*, 53:4978–4986 (Oct. 1993).
Hague et al., *Oncogene*, 9:3367–3370 (1994).
Henkart, *Immunity*, 1:343–346 (Aug. 1994).
Heusel et al., *Cell*, 76:977 (1994).
Hockenberry et al., *Cell*, 75:241–251 (Oct. 1993).
Hockenberry et al., *Nature*, 348:334–336 (Nov. 1990).
Kägi et al., *Science*, 265:528–530 (Jul. 1994).
Kägi et al., *Nature*, 369:31–37 (May 1994).
Kelekar et al., *Mol. Cell Biol.*, 17(12):7040–7046 (Dec. 1997).
Kitada et al., *Antisense Res. Dev.*, 4(2):71–79 (1994).
Littman, *Curr. Biol.*, 4(7):618–620 (1994).
Lotem et al., *Cell Growth Differ*, 4:41–47 (Jan. 1993).
Meng et al., *J. Comp. Chem.*, 15:505 (1992).
Miyashita et al., *Cancer Res.*, 52:5407–5411 (Oct. 1992).
Miyashita et al., *Blood*, 81(1):151–157 (Jan. 1993).
McDonnell et al., *Cancer Res.*, 52:6940–6944 (Dec. 1992).
Muchmore et al., *Nature*, 381:335–341 (May 1996).
Nuñez et al., *J. Immunol.*, 144(9):3602–3610 (1990).
Ohmori et al., *Biochem. Biophys. Res. Commun.*, 192(1):30–36 (Apr. 1993).
Sattler et al., *Science*, 275:983–986 (Feb. 1997).
Sato et al., *Proc. Natl. Acad. Sci. U.S.A.*, 91:9238–9242 (Sep. 1994).
Sedlak et al., *Proc. Natl. Acad. Sci. U.S.A.*, 92:7834–7838 (Aug. 1995).
Strasser et al., *Proc. Natl. Acad. Sci. U.S.A.*, 88(19):8661–8665 (Oct. 1991).
Vaux et al., *Nature*, 335:440–442 (Sep. 1988).
Veis et al., *Cell*, 75:229–40 (1993).
Webb et al., *Lancet*, 349:1137–1141 (Apr. 1997).
Yin et al., *Nature*, 369:321–323 (May 1994).

*Primary Examiner*—Dwayne C. Jones
(74) *Attorney, Agent, or Firm*—Drinker Biddle & Reath LLP

(57) ABSTRACT

Small molecule inhibitors of Bcl-2 function are used to induce apoptosis of cells which are subject to Bcl-2, which cells are otherwise subject to Bcl-2 mediated blockage of apoptosis. The compounds are useful for treating cancer, autoimmune disorders and viral infection.

13 Claims, 6 Drawing Sheets

SMALL MOLECULE INHIBITORS OF BCL-2 PROTEINS

CROSS-REFERENCE TO RELATED APPLICATIONS

This application claims priority from provisional applications Ser. No. 60/128,100, filed Apr. 7, 1999, and No. 60/093,561, filed Jul. 21, 1998, the entire disclosures of which are incorporated herein by reference.

FIELD OF THE INVENTION

The present invention generally relates to the field of oncology and inhibitors of Bcl-2 proteins, and more particularly to small molecule inhibitors of Bcl-2 proteins involved in mediating the death of cancer cells, virally infected cells and self-reactive lymphocytes.

BACKGROUND OF THE INVENTION

Bcl-2 (B cell lymphoma/leukemia 2) was originally identified at the chromosomal breakpoint of t(14;18)-bearing B-cell lymphomas. Bcl-2 is now known to belong to a growing family of proteins which regulate programmed cell death or apoptosis. The Bcl-2 family includes both death antagonists (Bcl-2, Bcl-$x_L$, Bcl-w, Bfl-1, Brag-1, Mcl-1 and Al) and death agonists (Bax, Bak, Bcl-$x_S$, Bad, Bid, Bik and Hrk) (Thompson, *Science* 267:1456–62 (1992); Reed, *J. Cell Biol.* 124:1–6 (1994); Yang et al., *Blood* 88:386–401 (1996)). This family of molecules shares four homologous regions termed Bcl homology (BH) domains BH 1, BH2, BH3, and BH4. All death antagonist members contain the BH4 domain while the agonist members lack BH4. It is known that the BH1 and BH2 domains of the death antagonists such as Bcl-2 are required for these proteins to heterodimerize with death agonists, such as Bax, and to repress cell death. On the other hand, the BH3 domain of death agonists is required for these proteins to heterodimerize with Bcl-2 and to promote apoptosis.

Programmed cell death or apoptosis plays a fundamental role in the development and maintenance of cellular homeostasis. Homologous proteins and pathways in apoptosis are found in a wide range of species, indicating that cellular demise is critical for the life and death cycle of the cell in all organisms. When extracellular stimuli switch on the cell-death signal, the response of the cell to such stimuli is specific for the particular cell type (Bonini et al., *Cell* 72:379–95 (1993)). The pathway to cellular suicide is controlled by certain checkpoints (Oltvai, *Cell* 79:189–92 (1994)). The Bcl family proteins, including both antagonists of apoptosis (such as Bcl-2) and agonists of apoptosis (such as Bax), constitute the primary checkpoint. As such, the transmission of a cell-death signal can be either promoted or blocked by the different combinations of the Bcl-2 family members. The three-dimensional structure of a death antagonist, Bcl-$X_L$, as determined by X-ray crystallography and NMR spectroscopy, provides a structural basis for understanding the biological functions of Bcl-2 family members and for developing novel therapeutics targeting Bcl-2 mediated apoptotic pathways (Muchmore et al., *Nature* 381:335–41 (1996)).

The detailed mechanism of Bcl-2 proteins in mediating molecular pathways of apoptosis has been the subject of intensive investigation. It is known that the apoptotic signaling pathway involves the activation of caspases which, once activated, cleave several cellular substrates such as poly(adenosine diphosphate-ribose) polymerase (PARP) and lead to final events of apoptosis. Bcl-2 plays a crucial role in regulating the process of apoptosis. One possible mechanism for Bcl-2 function is that Bcl-2 inhibits the release of cytochrome c from mitochondria. Cytochrome c is important for the activation of caspases. As such, Bcl-2 blocks caspase activation and subsequent events leading to apoptosis.

Being able to block apoptosis, Bcl-2 is known to contribute to neoplastic cell expansion by preventing normal cell turnover caused by physiological cell death mechanisms. High levels and aberrant patterns of Bcl-2 gene expression are found in a wide variety of human cancers, including ~30–60% of prostate, ~90% of colorectal, ~60% of gastric, ~20% of non-small cell lung cancers, ~30% of neuroblastomas, and variable percentages of melanomas, renal cell, and thyroid cancers, as well as acute and chronic lymphocytic and non-lymphocytic leukemias (Ellis et al., *Cell Biol.* 7, 663 (1991); Henkart, *Immunity* 1, 343 (1994)); Kägi et al., *Science* 265, 528 (1994); Kägi et al., *Nature* 369, 31 (1994); Heusel et al., *Cell* 76, 977 (1994)).

The expression levels of Bcl-2 protein also correlate with relative resistance to a wide spectrum of current chemotherapeutic drugs and γ-irradiation (Hanada et al., Cancer Res. 53:4978–86 (1993); Kitada et al., *Antisense Res. Dev.* 4:71–9 (1994); Miyashita et al., *Cancer Res.* 52:5407–11 (1992); Miyashita et al., *Blood* 81:151–7 (1993)). Since Bcl-2 can protect against such a wide variety of drugs which have very different mechanisms of action, it is possible that all these drugs use a common final pathway for the eventual induction of cell death which is regulated by Bcl-2. This notion is supported by the findings that chemotherapeutic drugs induce cell death through a mechanism consistent with apoptosis as opposed to necrosis. Therefore, Bcl-2 can inhibit the cell killing effect of currently available anticancer drugs by blocking the apoptotic pathway.

Because of its role in blocking apoptosis, Bcl-2 plays an important role in many types of cancer. As noted above, Bcl-2 blocks apoptosis, thereby preventing normal cell turnover. As a result, neoplastic cell expansion occurs unimpeded by the normal cellular turnover process. Prostate cancer is one particular example where Bcl-2 has important implication in the pathogenesis and treatment for a disease. Approximately 100,000 new cases of prostate cancer are diagnosed each year in the United States and about 30,000 deaths per year are attributable to this disease (Lynn et al., *JNCI* 87:867 (1995)). It has recently been found that hormone therapy-resistant prostate cancers express Bcl-2 (McDonnell et al., *Cancer Res.* 52:694–04 (1992)), while the normal prostate cells from which prostate cancers originate lack Bcl-2 (Colombel et al., *Am J Pathol* 143:390–400 (1993)). This indicates that Bcl-2 may protect prostate cancer cells from undergoing apoptosis induced by the anticancer drugs, such as Taxol (Haldar et al., *Cancer Res.*, 56:1235–5 (1996)). The clinical efficacy of nearly every cytotoxic anticancer drug currently available depends directly or indirectly on the assumption that tumor cells grow more rapidly than normal cells. However, this may not apply to human prostate cancer cells, which show very slow growth kinetics. Tumor kinetics studies have indicated that prostate cancer may be the consequence of the imbalance in cell turnover mechanisms more so than an increase in cell cycle rates. Thus, current anticancer drugs may not be effective in eradicating these nonproliferative prostate cancer cells.

The understanding of the biology of Bcl-2 in cancer and chemoresistance has opened new avenues in the development of novel anticancer strategies. One effective approach to overcome the chemoresistance of prostate cancers is to inhibit the protective function of Bcl-2 proteins. New drugs that modulate Bcl-2 mediated apoptotic response would represent a novel mechanism-based strategy for the treatment of prostate cancers and other cancers. Because the function of Bcl-2 is not absolutely necessary in many normal cell types (Veis et al., *Cell,* 75:229–40(1993)), a systematic inhibition of Bcl-2 may not affect the normal cellular function. This notion is supported by recent encouraging data from the clinical trial that antisense oligonucleotides targeted against the Bcl-2 gene can specifically inhibit non-Hodgkin's lymphoma in humans (Webb et al,. *Lancet* 349:1137–41 (1997)). However, the clinical value of such antisense oligonucleotides is limited by their lack of enzymatic stability, cell permeability, and oral activity. As discussed above, currently available anticancer drugs may not be effective due to the chemoresistance of prostate cancer cells. Therefore, there is an impending need for highly potent, cell permeable, and orally active Bcl-2 inhibitors as a new generation of effective therapeutics for the treatment of prostate cancer, as well as other cancers.

Compared to other therapeutics such as antibodies, peptides or antisense oligonucleotides, small organic drugs may possess several advantages in the clinical application: (1) they are less likely to be immunogenic; (2) they are likely to be stable and to be able to cross the cell membrane; (3) they are more likely to be administrable through the oral route, which is most desirable in terms of patient compliance; and (4) they are amenable to synthesis and modification which significantly lowers the cost of the therapeutic treatment.

SUMMARY OF THE INVENTION

It is an object of the invention to provide small molecule inhibitors of bcl-2 function useful in treatment of cancer, autoimmune disease and certain types of viral infection which are characterized by cellular signals which inhibit apoptosis.

It is an object of the invention to induce apoptosis of cells, particularly cancer cells, most particularly cancer cells which are regulated by Bcl-2.

It is an object of the invention to provide novel therapeutics and methods of treatment for reversing Bcl-2-mediated blockage of cell apoptosis in cancer cells.

It is an object to provide of the invention to overcome Bcl-2-mediated chemoresistance in tumor cells.

These and other objects of the invention are apparent from the following description.

A method of inducing apoptosis of cells regulated by Bcl-2 in a subject is provided. An effective amount of an active compound is administered to the subject. Preferably, the compound causes the fragmentation of DNA in a Bcl-2 transfected HL-60 cell line when incubated with such cells at a concentration of not more than 100 $\mu$M for 24 hours. In some embodiments, the compound is also characterized by a dissociation constant $K_D$ of not more than about 500 $\mu$M, preferably no more than about 100 $\mu$M, most preferably no more than about 10 $\mu$M, for binding the hydrophobic pocket on the Bcl-2 protein formed by the BH1, BH2, and BH3 domains.

By "regulated by Bcl-2" with respect to the condition of a cell is meant that the balance between cell proliferation and apoptotic cell death is controlled, at least in part, by Bcl-2. By "apoptotic cell death" is meant the programed death which results in controlled autodigestion of the cell, as opposed to necrotic cell death. Apoptotic cell death is characterized by cytoskeletal disruption, cell shrinkage, and membrane blebbing. The nucleus undergoes condensation and nuclear DNA becomes degraded and fragmented. Apoptosis is also characterized by loss of mitochondrial function. Necrotic cell death, on the other hand, is a pathological form of cell death resulting from acute cellular injury, which is typified by rapid swelling and lysis.

According to certain embodiments of the invention, the cells induced to undergo apoptosis comprise cancer cells, virus-infected cells or self-reactive lymphocytes. Thus, the active compounds are used to treat cancer, viral infection, or autoimmune disorders.

In another embodiment, a method of reversing Bcl-2-mediated blockage of apoptosis in cancer cells is provided by contacting such cells with an active compound of the invention. In another embodiment, a method is provided for treating a subject afflicted with a cancer characterized by cancer cells which express Bcl-2. The method comprises administering an effect amount of an active compound of the invention.

Active compounds which have a molecular weight in the range of from about 150 to about 500 daltons.

According to one embodiment of the invention, the compounds have the formula I:

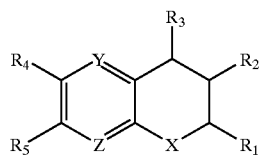

wherein:
X is selected from the group consisting of $CH_2$; $CHOCH_3$; NH; O and S;

Y and Z are independently selected from the group consisting of CH and N; and when Z is N, then Y may further be —$CR_6$, where $R_6$ is selected from the group consisting of $CH_3$; $OCH_3$; $CNH_2$; and COH;

$R_1$ is selected from the group consisting of hydrogen; $C_{1-5}$ alkyl; $C_{1-5}$ alkoxy; OH; $NH_2$; $NO_2$; CHO; $COCH_3$; COOH; $COOCH_3$; $N(C_{1-3}$ alkyl$)_2$; $NH(C_{1-3}$ alkyl); $OCOCH_3$; $OCOCH_2CH_3$; $NHCOCH_3$; $NHNHCOCH_3$; $NHNHCONH_2$; phenyl; phenyl which is mono-, di-, or tri-substituted with $NH_2$, OH, halogen, $NO_2$, $CF_3$, COOH or $COOCH_3$; cyclohexyl; cyclohexyl which is mono-, di-, ortri-substituted with $NH_2$, OH, halogen or $CF_3$; and five- and six-member heterocyclic rings, preferably a heterocyclic ring selected from the group consisting of piperidino, piperazino, morpholino, pyrimidyl, pyrrolidino and imidazo;

$R_2$ is selected from the group consisting of hydrogen; $C_{1-3}$ alkyl; $C_{1-3}$ alkoxy; halogen; $CF_3$; $NH_2$; OH; COOH; $COOCH_3$; $CONH_2$; and $CONHCH_3$;

or, $R_1$ and $R_2$ together may form the group —$CH_2CH_2CH_2$— or —$CH_2CH_2CH_2CH_2$—;

or, $R_1$ and $R_2$ together may form, starting from $R_1$, the group —$NHCH_2CH_2$—, —$NHCOCH_2$—, or —$OCOCH_2$—;

$R_3$ is selected from the group consisting of H; $CH_3$; $CF_3$; $OCH_3$; $NH_2$; OH; COOH; $COCH_3$; CH═$CH_2$; $CH_2$═$CHCH_2$; $CH(CH_3)_2$; $CH_2OH$; $CH_2NH_2$; $CH_2COOH$; cyclohexyl; cyclohexyl which is mono-, di-, or tri-substituted with $NH_2$, OH, halogen, $OCH_3$ or $CF_3$; five- and six-member heterocyclic rings, preferably a heterocyclic ring selected from the group consisting of piperidinyl, piperazinyl, morpholino, pyrimidyl, pyrrolyl, pyrrolidino, and imidazyl; and a substituted phenyl group of the formula:

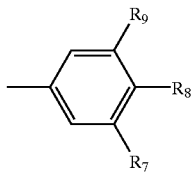

wherein $R_7$, $R_8$ and $R_9$ are independently selected from the group consisting of hydrogen, $CH_3$, $CF_3$, OH, $OCH_3$, $CH_2OH$ and CHO; provided that at least two of the members of the group $R_7$, $R_8$ and $R_9$ must be OH or $OCH_3$ when the remaining member of the group is hydrogen, $CH_3$ or $CF_3$;

$R_4$ and $R_5$ are independently selected from the group consisting of hydrogen, $CH_3$, and $OCH_3$; and when Y and Z are both CH, $R_4$ and $R_5$ may be further selected from OH and $NH_2$;

or, $R_4$ and $R_5$ together may form the group —$CH_2CH_2CH_2$— or —$HH_2CH_2CH_2CH_2$—;

or, $R_4$ and $R_5$ together may form, starting from $R_4$, the group —$NHCH_2CH_2$—, —$NHCOCH_2$—, —$OCOCH_2$— or —$O(CH_2)_n$—O—, wherein n is 1, 2 or 3;

or a pharmaceutically acceptable salt thereof when the compound includes at least one $NH_2$ or COOH substituent.

Preferably, $R_2$ is $CH_3$, $CH_2CH_3$, COOH, $COOCH_3$, $CONH_2$, or $CONHCH_3$.

Preferably, $R_7$, $R_8$ and $R_9$ are all $OCH_3$; or $R_7$ and $R_9$ are $OCH_3$, and $R_8$ is OH.

When $R_1$ or $R_3$ is substituted cyclohexyl, the preferred position of the substitution is para. Likewise, when $R_1$ is substituted phenyl, the preferred position of the substitution is para.

The preferred group corresponding to $R_3$ in formula I is the substituted phenyl group of the formula:

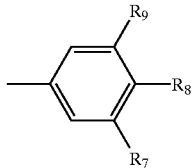

Preferred compounds according to formula I include the compounds identified as HA11-1 through HA11-73, listed in Table 1, below. Most preferred compounds according to formula I include HA11-57 and HA11-17:

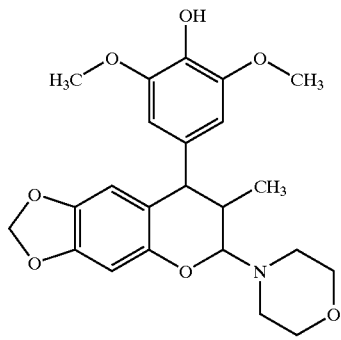

HA11-57

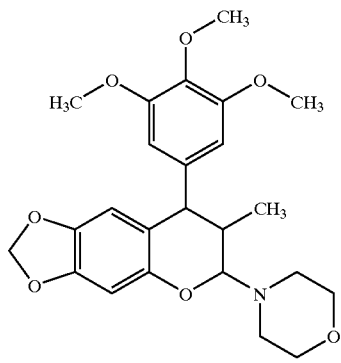

HA11-17

According to another embodiment of the invention, the active compounds have the formula II:

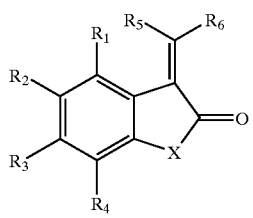

II wherein $R_1$, $R_2$, $R_3$ and $R_4$ are independently selected from the group consisting of hydrogen; $C_{1-5}$ alkyl; $C_{1-5}$ alkoxy; OH; $NH_2$; $NO_2$; CHO; $COCH_3$; COOH; $COOCH_3$; $N(C_{1-3}$ alkyl$)_2$; and $NH(C_{1-3}$ alkyl); and one of $R_1$, $R_2$, $R_3$ and $R_4$ may be phenyl or a heterocyclic ring, preferably a heterocyclic ring selected from the group consisting of piperidino, piperazino, morpholino, pyrimidyl, pyrrolidino and imidazo; provided at least one of $R_1$, $R_2$, $R_3$ and $R_4$ must be hydrogen;

$R_5$ and $R_6$ are independently selected from the group consisting of hydrogen; CN; $CH_2CN$; $COOCH_3$; $CONH_2$; phenyl; phenyl which is mono-, di-, or tri-substituted with $NH_2$, OH, halogen, $NO_2$, $CH_3$, $OCH_3$, $CF_3$, COOH or $COOCH_3$; cyclohexyl; cyclohexyl which is mono-, di-, or tri-substituted with $NH_2$, OH, halogen or $CF_3$; and five- and six-member heterocyclic rings, preferably a heterocyclic ring selected from the group consisting of pyrrolyl, imidazolyl, piperidinyl, piperazinyl, morpholino, pyrimidyl and pyrrolidino; provided, only one of $R_5$ or $R_6$ may be phenyl, substituted phenyl, cyclohexyl, substituted cyclohexyl or heterocyclic in the same compound, and further provided that when one of $R_5$ or $R_6$ is phenyl, substituted phenyl, cyclohexyl, substituted cyclohexyl or heterocyclic, then the other must be hydrogen;

or at least one of $R_5$ and $R_6$ may be halogen, provided that the other must be $C_{1-5}$ alkyl or $C_{1-5}$ alkoxy.

or a pharmaceutically acceptable salt thereof when the compound includes at least one $NH_2$ or COOH substituent.

When $R_5$ or $R_6$ is substituted phenyl or substituted cyclohexyl, in formula II, the preferred position of the substitution is para.

Preferred compounds according to formula II include the compounds identified as HA12-3 and HA12-16 (compound HA12-16 may also be identified herein as "HA01"):

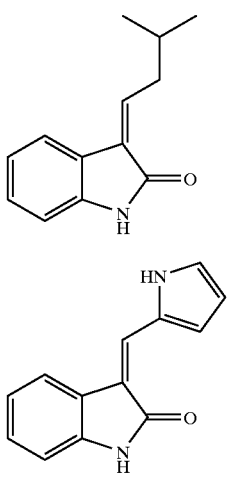

In the compounds of formula I and II, where halogen substitution is possible, chorine, fluorine and bromine are preferred, with fluorine being most preferred.

According to another embodiment of the invention, the active compounds have the formula III:

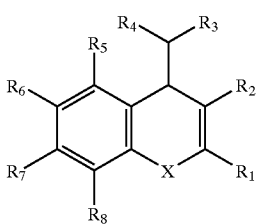

wherein:

X is selected from the group consisting of $CH_2$; $CHOCH_3$; NH; $NCH_3$; O; and S;

$R_1$ is selected from the group consisting of OH; $NH_2$; CHO; $COCH_3$; COOH; $N(C_{1-3}$ alkyl$)_2$; $NH(C_{1-3}$ alkyl); $OCOCH_3$; $OCOCH_2CH_3$; $NHCOCH_3$; $NHNHCOCH_3$; $NHNHCONH_2$; $N(C_{1-3}$alkyl$)_2$; $NH(C_{1-3}$ alkyl); and five- and six-member heterocyclic rings, preferably a heterocyclic ring selected from the group consisting piperidinyl, piperazinyl, morpholino, pyrimidyl, pyrrolyl, pyrrolidino and imidazyl;

$R_2$ is selected from the group consisting of $C_{1-3}$ alkyl; $C_{1-3}$alkoxy; OH; $NH_2$; CHO; $COCH_3$; $OCOCH_3$; $OCOCH_2CH_3$; COOH; $COOCH_3$; $COOCH_2CH_3$; $COOCH_2CH_2CH_3$;

$R_3$ is selected from the group consisting of $C_{1-3}$ alkyl; $C_{1-3}$ alkoxy; CN; $CH_2CN$; $CH_2NO_2$; CHO; $COCH_3$; COOH; $OCOCH_3$; $OCOCH_2CH_3$; $NHCOCH_3$; $NHNHCOCH_3$; $NHNHCONH_2$; $CH=CH_2$; $CH_2CH=CH_2$; $CH_2CHO$; and five- and six-member heterocyclic rings, preferably a heterocyclic ring selected from the group consisting piperidinyl, piperazinyl, morpholino, pyrimidyl, pyrrolyl, pyrrolidino and imidazyl;

$R_4$ is selected from the group consisting of $C_{1-3}$ alkyl; $C_{1-3}$ alkoxy; CN; $CH_2CN$; $CH_2NO_2$; CHO; $COCH_3$; $COCH_3$; COOH; $COOCH_3$;$COOCH_2CH_3$; $COOCH_2CH_2CH_3$; $OCOCH_3$; $OCOCH_2CH_3$;

$R_5$ is selected from the group consisting of hydrogen $CH_3$; $OCH_3$; OH: $NH_2$; Br; Cl; and F; and $R_6$, $R_7$ and $R_8$ are selected from the group consisting of hydrogen, $CH_3$; $CH_2CH_3$; $CF_3$; $NH_2$; OH; $OCH_3$; CN; $NO_2$; Cl; Br; F; COOH; and $COOCH_3$; provided, at least one member of the group $R_6$, $R_7$ or $R_8$ must be Cl, Br or F when the remaining members of said group are hydrogen;

or a pharmaceutically acceptable salt thereof when the compound includes at least one $NH_2$ or COOH substituent.

Preferred for formula III are the following:

$R_1$: $NH_2$; $N(C_{1-3}$ alkyl$)_2$; and $NH(C_{1-3})$alkyl; piperidinyl; piperazinyl; morpholino; pyrimidyl; pyrrolyl; pyrrolidino; and imidazyl;

$R_2$: $COCH_3$; $OCOCH_3$; $OCOCH_2CH_3$; COOH; $COOCH_3$; $COOCH_2CH_3$; and $COOCH_2CH_2CH_3$;

$R_3$: CN; $CH_2CN$; $CH_2NO_2$; $CH=CH_2$; $CH_2CH=CH_2$; and $CH_2CHO$;

$R_4$: $COCH_3$; $OCOCH_3$; $OCOCH_2CH_3$; COOH; $COOCH_3$; $COOCH_2CH_3$; and $COOCH_2CH_2CH_3$;

$R_5$: hydrogen, Br; Cl; and F;

$R_6$, $R_7$ and $R_8$: $NH_2$; OH; $OCH_3$; CN; $NO_2$; Cl; Br and F.

When $R_6$, $R_7$ or $R_8$ are Br, Cl or $OCH_3$, the preferred positions of the substitution are $R_6$ and $R_8$.

According to another embodiment of the invention, the active compound for use in the method of the invention is selected from the group consisting of compounds HA13, HA14, HA02, HA03 and HA04:

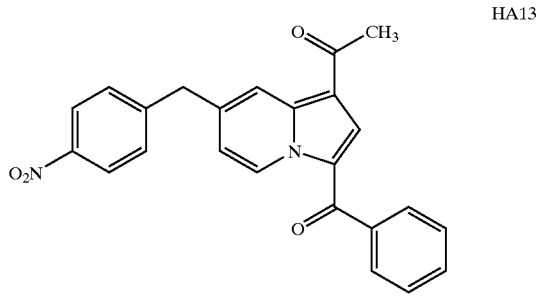

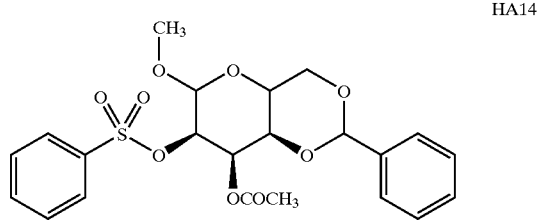

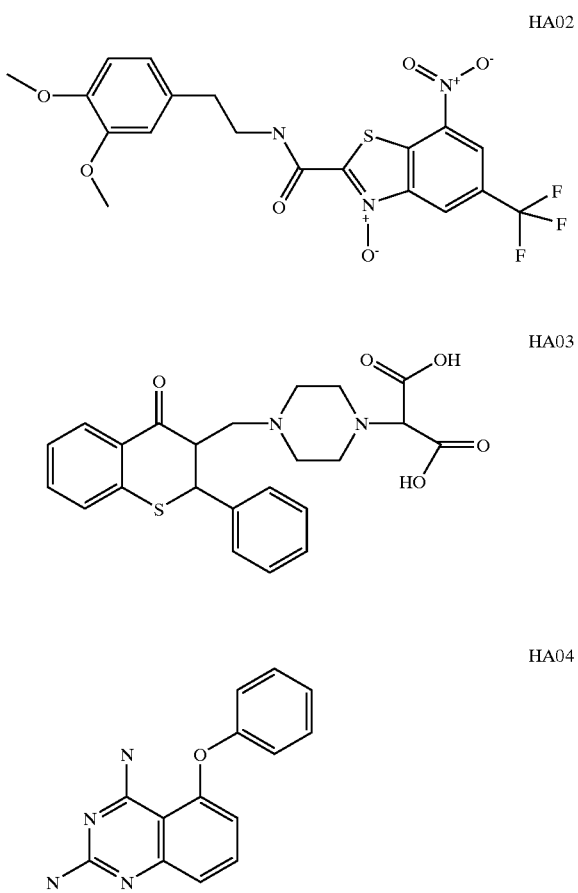

DESCRIPTION OF THE FIGURES

FIG. 2 also shows the binding of Bcl-2 protein to fluorescein-labeled peptides derived from CD4 (Flu-1250 and Flu-1251) and Bcr-Abl SH3 (Flu-1217). The lack of binding interaction detected in these control systems (the signals were close to the background level of free Flu-1193 (Flu-1193 alone)), demonstrates the specificity of the binding of Flu-1193 to Bcl-2.

DETAILED DESCRIPTION OF THE INVENTION

Figure 1:
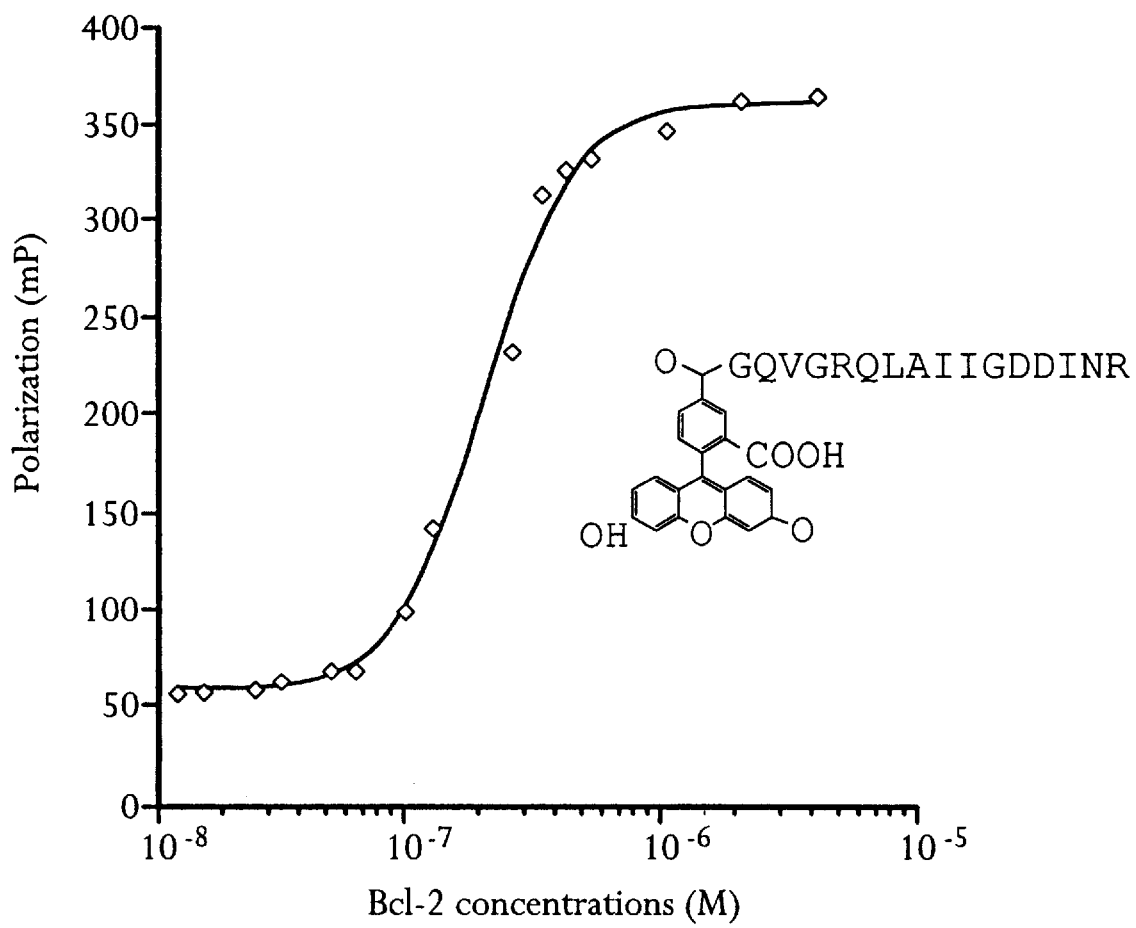
FIG. 1 is a plot of the binding of fluorescein-labeled peptide 1193 with Bcl-2 protein.

A computer screening technique has been employed to discover a novel class of small organic compounds as potent Bcl-2 inhibitors and new anticancer agents. The three dimensional structure of Bcl-2 was constructed based on the X-ray and NMR structure of the highly homologous protein Bcl-$x_L$ (>98% sequence homology to Bcl-2 in the four functionally important BH domains) published by others (McDonnell et al., Cancer Res. 52:6940 (1992); Hague et al., Oncogene 9, 3367 (1994); Castle et al., Am. J. Pathol 143, 1543 (1993); Littman, Curr. Biol. 4:618 (1994)). A hydrophobic binding pocket was found in the structure of Bcl-2 which is formed by the BH1, BH2, and BH3 domains. A highly sensitive Bcl-2 ligand binding assay was then employed to test these compounds for specific binding to the hydrophobic surface pocket. This pocket is required for the anti-apoptotic function of Bcl-2; a variety of mutations at his site have been shown to inhibit function of Bcl-2 proteins (Yin et al., Nature 369:321–3, 1994).

Molecular Modeling

DOCK3.5 is an automatic algorithm to screen small-molecule databases for ligands that could fit a given receptor. Meng et al., J. Comp. Chem. 15:505 (1992). The program exploits a geometric description of the surface of the target molecule to define plausible binding pockets. To exploit this approach, a "negative image" of the ligand binding pocket on the protein surface is created. The image is created by the computational equivalent of placing atom-sized spheres into the binding pocket. A representative set of spheres are identified by DOCK3.5 that fit extremely well into the binding pocket. The generated spheres constitute an irregular grid that is matched to the atomic centers of potential ligands. The list of atom centers, or more conveniently the matrix of interatomic distances linking these atom centers forms a useful description of the binding site. The matrix of interatomic distances for the putative ligand is also made. The best mutual overlap of the two matrices is sought. This alignment specifies the orientation of the ligand relative to the negative image of the protein and thus docks the ligand into the protein's binding pocket.

The DOCK3.5 compound was used to screen the 150,000 compounds contained in the Available Chemicals Dictionary (Molecular Design Limited, San Leonadro, Calif.) as potential ligands for the Bcl-2 binding pocket. Both shape complementarity and electrostatic interactions with the Bcl-2 binding pocket were used as scoring criteria. On a computer, these compounds were then visually screened three times independently in the context of the Bcl-2 binding pocket. The result is the compounds compiled in Table 1. Screening also identified compounds HA02, HA03 and HA04. The compounds identified as "RCL__" in Table I are available from Molecular Design Limited. Compounds HA02, HA03 and HA04 are also commercially available.

TABLE I
Compounds for formula I
| Comp. Number | MOLNAME | M.W | MOLSTRUCTURE |
|---|---|---|---|
| HA11-1 | MILLETTONE | 378.378 | 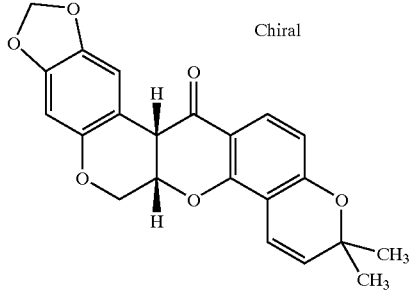 |
| HA11-2 | 9-(2,4-DI-MEO-PH)-5A-MEO-4H-1,3,5,7-TETRAOXA-DICYCLOPENTA(B,G)NAPHTHALEN-8-ONE | 400.381 | 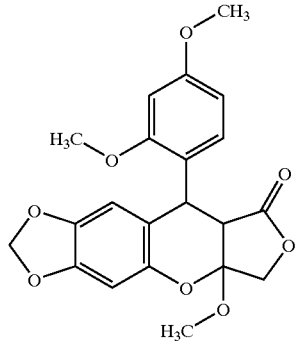 |
| HA11-3 | 1-(10-(2,4-DIMETHOXY-PH)-1,3,5-TRIOXA-CYCLOPENTA(B)ANTHRACEN-5A-YL)-PYRROLIDINE | 437.533 | 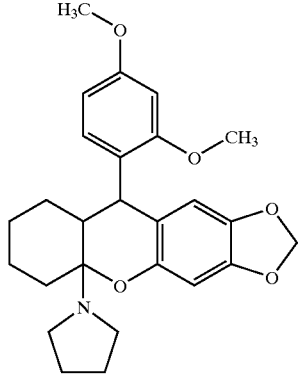 |
| HA11-4 | 5A-MEO-9-(2-MEO-PH)-4H-1,3,5,7-TETRAOXA-DICYCLOPENTA(B,G)NAPHTHALEN-8-ONE | 370.355 | 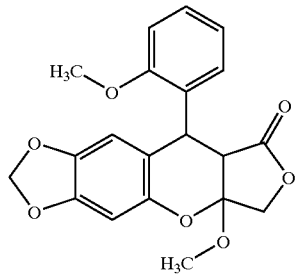 |

TABLE I-continued

_Compounds for formula I_

| Comp. Number | MOLNAME | M.W | MOLSTRUCTURE |
|---|---|---|---|
| HA11-5 | 6-MEO-6,7-DIMETHYL-8-(3,4,5-TRIMETHOXY-PH)-7,8-2H-6H-(1,3)DIOXOLO(4,5-G)CHROMENE | 402.44 | |
| HA11-6 | 8-(4-HO-3,5-DIMETHOXY-PH)-7-ME-7,8-DIHYDRO-6H-[1,3]DIOXOLO[4,5-G]CHROMEN-6-OL | 360.36 | |
| HA11-7 | 6-HO-6-ME-8-(TRI-MEO-PH)-[1,3]DIOXOLO[4,5-G]CHROMENE-7-CARBOXYLIC ACID ET ESTER | 446.449 | |
| HA11-8 | RCL R17,027-5 | 431.443 | |

TABLE I-continued

Compounds for formula I

| Comp. Number | MOLNAME | M.W | MOLSTRUCTURE |
|---|---|---|---|
| HA11-9 | RCL R17,028-3 | 455.504 | |
| HA11-10 | 1-[6-ME-8-(3,4,5-TRI-MEO-PH)-2H-6H-[1,3] DIOXOLO[4,5-G]CHROMEN-6-YL]-PYRROLIDINE | 427.494 | |
| HA11-11 | 6-MEO-8-(4-METHOXY-PHENYL)-6-METHYL-7,8-DIHYDRO-6H-[1,3]DIOXOLO[4,5-G]CHROMENE | 328.362 | |
| HA11-12 | 6-ME-8-(3,4,5-TRIMETHOXY-PHENYL)7,8-DIHYDRO-6H-[1,3]DIOXOLO[4,5-G]CHROMEN-6-OL | 374.387 | |

TABLE I-continued

Compounds for formula I

| Comp. Number | MOLNAME | M.W | MOLSTRUCTURE |
|---|---|---|---|
| HA11-13 | 8-(2-HYDROXY-PHENYL)-7-METHYL-7,8-DIHYDRO-6H-[1,3]DIOXOLO[4,5-G]CHROMEN-6-OL | 300.308 | |
| HA11-14 | 8-(4-HO-3,5-DIMETHOXY-PH)-6-ME-7,8-DIHYDRO-6H-[1,3]DIOXOLO[4,5-G]CHROMEN-6-OL | 360.36 | |
| HA11-15 | 9-(3-MEO-PH)-5A,6,8A,9-4H-1,3,5,7-TETRAOXA-DICYCLOPENTA[B,G]NAPHTHALEN-8-ONE | 340.329 | |
| HA11-16 | 1-[8-(2,4-DI-MEO-PH)-7-ME-7,8-2H-6H-[1,3]DIOXOLO[4,5-G]CHROMEN-6-YL]PYRROLIDINE | 397.468 | |

TABLE I-continued

Compounds for formula I

| Comp. Number | MOLNAME | M.W | MOLSTRUCTURE |
|---|---|---|---|
| HA11-17 | 4-[7-ME-8-(3,4,5-TRI-MEO-PH)-2H-6H-[1,3] DIOXOLO[4,5-G]CHROMEN-6-YL]-MORPHOLINE | 443.493 | |
| HA11-18 | 1-[8-(3-MEO-PH)-6,7-DI-ME-7,8-2H-6H-[1,3] DIOXOLO[4,5-G]CHROMEN-6-YL]-PYRROLIDINE | 381.469 | |
| HA11-19 | 2-MEO-6-(6-ME-6-PYRROLIDIN-1-YL-2H-6H-[1,3] DIOXOLO[4,5-G]CHROMEN-8-YL)-PHENOL | 383.441 | |
| HA11-20 | 9-(4-MEO-PH)-5A,6,8A,9-4-1,3,5,7-TETRAOXA-DICYCLOPENTA[B,G]NAPHTHALEN-8-ONE | 340.329 | |

TABLE I-continued
Compounds for formula I
| Comp. Number | MOLNAME | M.W | MOLSTRUCTURE |
|---|---|---|---|
| HA11-21 | (4-MEO-PH)-[7-ME-8-(3,4,5-TRI-MEO-PH)-6H-[1,3]DIOXOLO[4,5-G]CHROMEN-6-YL]-AMINE | 479.526 | 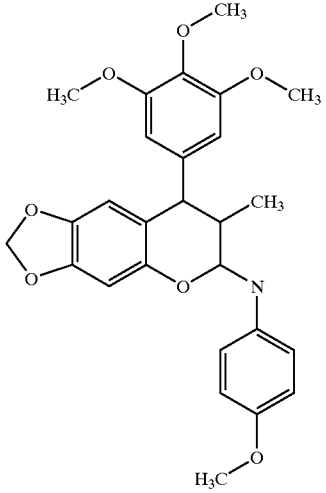 |
| HA11-22 | DI-ME-[4-(6-ME-6-PYRROLIDIN-1-YL-6H-[1,3]DIOXOLO[4,5-G]CHROMEN-8-YL)-PH]-AMINE | 380.485 | 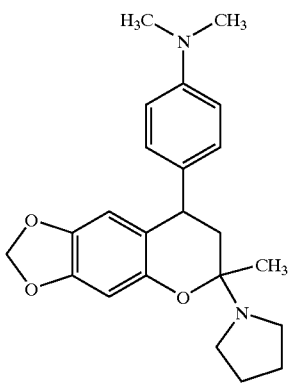 |
| HA11-23 | 1-[6-HO-8-(4-HO-3,5-DI-MEO-PH)-6-ME-6H[1,3]DIOXOLO[4,5-G]CHROMEN-7-YL]-ETHANONE | 402.397 | 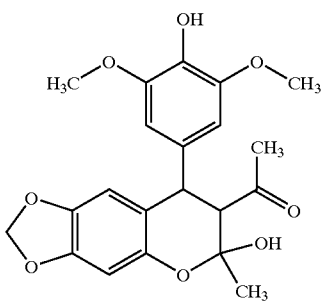 |

TABLE I-continued

Compounds for formula I

| Comp. Number | MOLNAME | M.W | MOLSTRUCTURE |
|---|---|---|---|
| HA11-24 | 1-[8-(2,4-DI-MEO-PH)-6,7-DI-ME-6H-[1,3]DIOXOLO[4,5-G]CHROMEN-6-YL]-PYRROLIDINE | 411.495 | |
| HA11-25 | 8-(4-METHOXY-PHENYL)-6,7-DIMETHYL-7,8-DIHYDRO-6H-[1,3]DIOXOLO[4,5-G]CHROMEN-6-OL | 328.362 | |
| HA11-26 | 6,7-DIMETHYL-8-(3,4,5-TRIMETHOXY-PH)-7,8-2H-6H-[1,3]DIOXOLO[4,5-G]CHROMEN-6-OL | 388.414 | |
| HA11-27 | 5A-HO-10-(3,4,5-TRI-MEO-PH)-HEXAHYDRO-1,3,5-TRIOXA-CYCLOPENTA[B]ANTHRACEN-9-ONE | 428.435 | |

TABLE I-continued

Compounds for formula I

| Comp. Number | MOLNAME | M.W | MOLSTRUCTURE |
|---|---|---|---|
| HA11-28 | 10-(2,4-DIMETHOXY-PH)-5A-HO-HEXAHYDRO-1,3,5-TRIOXA-CYCLOPENTA[B]ANTHRACEN-9-ONE | 398.409 | |
| HA11-29 | 2-MEO-6-(7-ME-6-PYRROLIDIN-1-YL-2H-6H-[1,3]DIOXOLO[4,5-G]CHROMEN-8-YL)-PHENOL | 383.441 | |
| HA11-30 | 6-(4-MEO-PH)-7-[3-(4-MEO-PH)-ALLYL]-7,8-DIHYDRO-6H-[1,3]DIOXOLO[4,5-G]CHROMENE | 430.497 | |
| HA11-31 | 8-(2-HO-3-MEO-PHENYL)-6-METHYL-7,8-DIHYDRO-6H-[1,3]DIOXOLO[4,5-G]CHROMEN-6-OL | 330.334 | |

TABLE I-continued

Compounds for formula I

| Comp. Number | MOLNAME | M.W | MOLSTRUCTURE |
|---|---|---|---|
| HA11-32 | RCL R17,093-3 | 469.531 | |
| HA11-33 | RCL R17,094-1 | 439.505 | |
| HA11-34 | 9-(3,4,5-TRI-MEO-PH)-4H-5AH-1,3,5-TRIOXA-DICYCLOPENTA[B,G]NAPHTHALEN-8-ONE | 398.409 | |

TABLE I-continued

Compounds for formula I

| Comp. Number | MOLNAME | M.W | MOLSTRUCTURE |
|---|---|---|---|
| HA11-35 | RCL R17,0976 | 528.579 | |
| HA11-36 | 1-[8-(4-DI-ME-AMINO-PH)-6-HO-6-ME-6H-[1,3]DIOXOLO[4,5-G]CHROMEN-7-YL]-ETHANONE | 369.415 | |
| HA11-37 | RCL R17,106-9 | 403.428 | |
| HA11-38 | 8-(2-HO-3-MEO-PHENYL)-7-METHYL-7,8-DIHYDRO-6H-[1,3]DIOXOLO[4,5-G]CHROMEN-6-OL | 330.334 | |

TABLE I-continued

Compounds for formula I

| Comp. Number | MOLNAME | M.W | MOLSTRUCTURE |
|---|---|---|---|
| HA11-39 | RCL R17,118-2 | 469.531 | |
| HA11-40 | N-PH-N'-[8-(3,4,5-TRI-MEO-PH)-2H-6H-[1,3] DIOXOLO[4,5-G]CHROMEN-6-YL]-HYDRAZINE | 450.488 | |
| HA11-41 | 2,6-DI-MEO-4-(7-ME-6-PIPERIDIN-1-YL-6H-[1,3] DIOXOLO[4,5-G]CHROMEN-8-YL)-PHENOL | 427.494 | |
| HA11-42 | 1-[7-ET-8-(3,4,5-TRI-MEO-PH)-2H-6H-[1,3] DIOXOLO[4,5-G]CHROMEN-6-YL]-PYRROLIDINE | 441.521 | |

TABLE I-continued

Compounds for formula I

| Comp. Number | MOLNAME | M.W | MOLSTRUCTURE |
|---|---|---|---|
| HA11-43 | 5A-HO-9-(HO-3,5-DI-MEO-PH)-4H-1,3,5,7-TETRAOXA-DICYCLOPENTA[B,G]NAPHTHALEN-8-ONE | 402.353 | |
| HA11-44 | 6-CYCLOHEXYLAMINO-8-(3,4,5-TRI-MEO-PH)-7,8-2H-6H-[1,3]DIOXOLO[4,5-G]CHROMEN-6-OL | 457.52 | |
| HA11-45 | RCL R17,135-2 | 458.417 | |
| HA11-46 | 2,6-DI-MEO-4-(7-ME-6-PYRROLIDIN-1-YL-6H-[1,3]DIOXOLO[4,5-G]CHROMEN-8-YL]-PHENOL | 413.467 | |

TABLE I-continued
Compounds for formula I
| Comp. Number | MOLNAME | M.W | MOLSTRUCTURE |
|---|---|---|---|
| HA11-47 | RCL R17,138-7 | 420.55 | 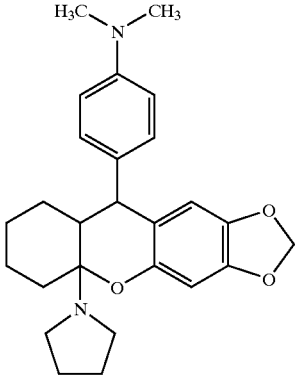 |
| HA11-48 | 7-ME-8-(3,4,5-TRIMETHOXY-PHENYL)-7,8-DIHYDRO-6H-[1,3]DIOXOLO[4,5-G]CHROMEN-6-OL | 374.387 | 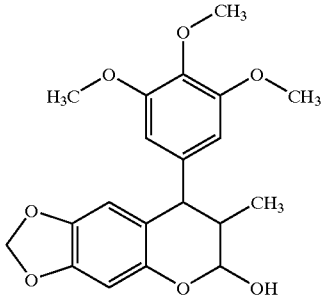 |
| HA11-49 | 6-MEO-8-(4-MEO-PHENYL)-6,7-DIMETHYL-7,8-DIHYDRO-6H-[1,3]DIOXOLO[4,5-G]CHROMENE | 342.389 | 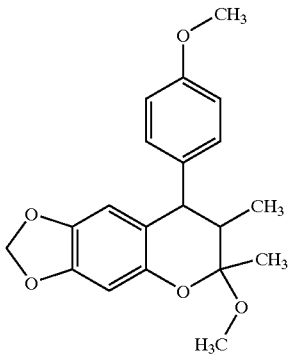 |
| HA11-50 | 8-(2,3-DIMETHOXY-PHENYL)-7-METHYL-7,8-DIHYDRO-6H-[1,3]DIOXOLO[4,5-G]CHROMEN-6-OL | 344.361 | 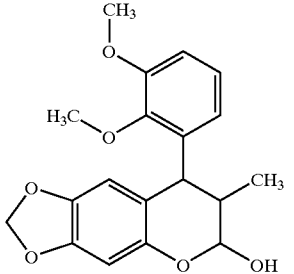 |

TABLE I-continued

Compounds for formula I

| Comp. Number | MOLNAME | M.W | MOLSTRUCTURE |
|---|---|---|---|
| HA11-51 | RCL R17,150-6 | 460.476 | |
| HA11-52 | 1-[7-ME-8-(3,4,5-TRI-MEO-PH)-2H-6H-[1,3]DIOXOLO[4,5-G]CHROMEN-6-YL]-PYRROLIDINE | 427.494 | |
| HA11-53 | RGL R17,155-7 | 426.462 | |
| HA11-54 | 2-(7-ME-6-MORPHOLIN-4-YL-7,8-DIHYDRO-6H-[1,3]DIOXOLO[4,5-G]CHROMEN-8-YL)-PHENOL | 369.415 | |

TABLE I-continued

Compounds for formula I

| Comp. Number | MOLNAME | M.W | MOLSTRUCTURE |
|---|---|---|---|
| HA11-55 | RCL R17,160-3 | 407.507 | |
| HA11-56 | 8-(2-HO-3-MEO-PH)-6,7-DIMETHYL-7,8-DIHYDRO-6H-[1,3]DIOXOLO[4,5-G]CHROMEN-6-OL | 344.361 | |
| HA11-57 | 2,6-DI-MEO-4-(7-ME-6-MORPHOLIN-4-YL-6H-[1,3]DIOXOLO[4,5-G]CHROMEN-8-YL)-PHENOL | 429.466 | |
| HA11-58 | 2-(6,7-DI-ME-6-PYRROLIDIN-1-YL-6H-[1,3]DIOXOLO[4,5-G]CHROMEN-8-YL)-6-MEO-PHENOL | 397.468 | |

TABLE I-continued

Compounds for formula I

| Comp. Number | MOLNAME | M.W | MOLSTRUCTURE |
|---|---|---|---|
| HA11-59 | RCL R17,171-9 | 452.548 | |
| HA11-60 | 1-[8-(4-MEO-PH)-6-ME-7,8-DIHYDRO-6H-[1,3]DIOXOLO[4,5-G]CHROMEN-6-YL]-PYRROLIDINE | 367.443 | |
| HA11-61 | 6-ETHOXY-6,7-DIMETHYL-8-(3,4,5-TRI-MEO-PH)-7,8-2H-6H-[1,3]DIOXOLO[4,5-G]CHROMENE | 416.467 | |

TABLE I-continued
Compounds for formula I
| Comp. Number | MOLNAME | M.W | MOLSTRUCTURE |
|---|---|---|---|
| HA11-62 | RCL R17,174-3 | 467.559 | 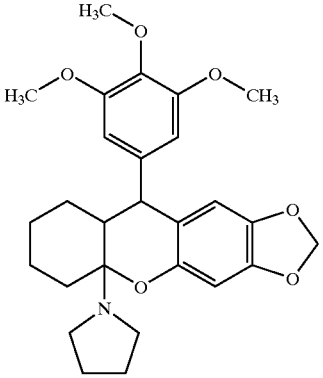 |
| HA11-63 | 5A-HO-10-(4-MEO-PH)-HEXAHYDRO-1,3,5-TRIOXA-CYCLOPENTA[B]ANTHRACEN-9-ONE | 368.383 | 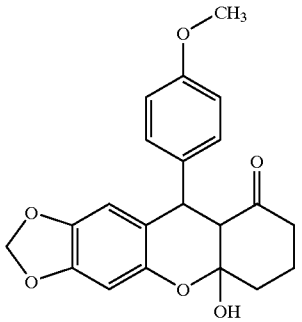 |
| HA11-64 | RCL R17,178-6 | 499.557 | 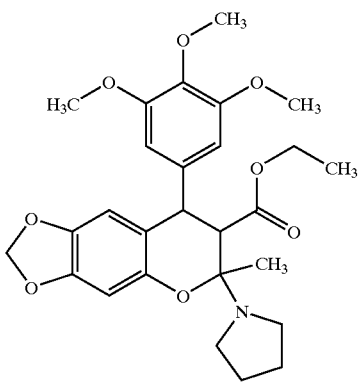 |
| HA11-65 | 8-(2-METHOXY-PHENYL)-6,7-DIMETHYL-7,8-DIHYDRO-6H-[1,3]DIOXOLO[4,5-G]CHROMEN-6-OL | 328.362 | 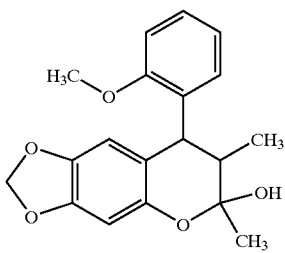 |

TABLE I-continued
Compounds for formula I
| Comp. Number | MOLNAME | M.W | MOLSTRUCTURE |
|---|---|---|---|
| HA11-66 | 1-[8-(4-MEO-PH)-6,7-DI-ME-7,8-2H-6H-[1,3]DIOXOLO[4,5-G]CHROMEN-6-YL]-PYRROLIDINE | 381.469 | 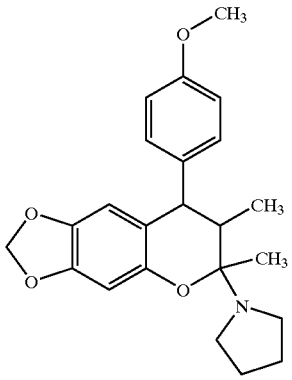 |
| HA11-67 | 1-[8-(4-MEO-PH)-7-ME-7,8-DIHYDRO-6H-[1,3]DIOXOLO[4,5-G]CHROMEN-6-YL]-PYRROLIDINE | 367.443 | 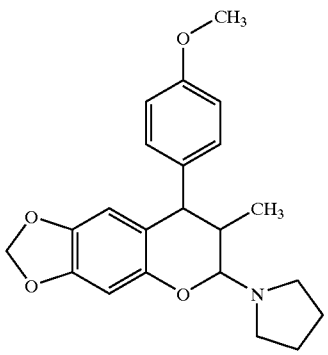 |
| HA11-68 | RCL R17,204-9 | 456.488 | 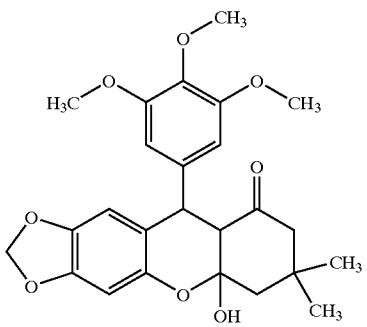 |
| HA11-69 | 1-[HO-6-ME-8-(3,4,5-TRI-MEO-PH)2H-6H-[1,3]DIOXOLO[4,5-G]CHROMEN-7-YL]ETHANONE | 416.424 | 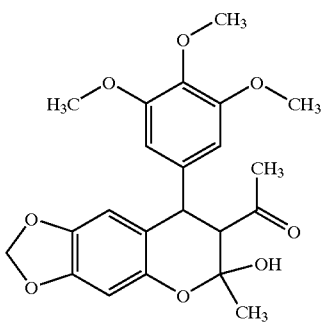 |

TABLE I-continued

Compounds for formula I

| Comp. Number | MOLNAME | M.W | MOLSTRUCTURE |
|---|---|---|---|
| HA11-70 | 8-(3-METHOXY-PHENYL)-6-METHYL-7,8-DIHYDRO-6H-[1,3]DIOXOLO[4,5-G]CHROMEN-6-OL | 314.335 | |
| HA11-71 | 1-[6,7-DI-ME-8-(3,4,5-TRI-MEO-PH)-6H-[1,3]DIOXOLO[4,5-G]CHROMEN-YL]-PYRROLIDINE | 441.521 | |
| HA11-72 | 8-(2,4-DIMETHOXY-PH)-6-MEO-6,7-DIMETHYL-7,8-2H-6H-[1,3]DIOXOLO[4,5-G]CHROMENE | 372.415 | |
| HA11-73 | RCL R17,216-2 | 453.532 | |

Preferred compounds according to formula III

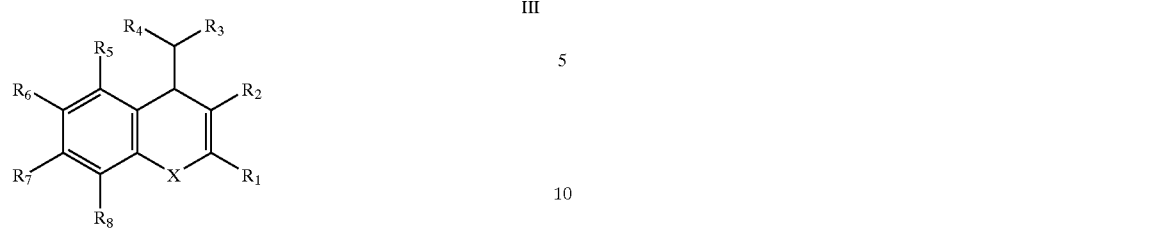

include the compounds of Table II:

TABLE II

Compounds for formula III

| Comp. Number | MOLNAME | M.W. | MOLSTRUCTURE |
|---|---|---|---|
| HA14-1 | ETHYL 2-AMINO-6-BROMO-4-(1-CYANO-2-ETHOXY-2-OXOETHYL)-4H-CHROMENE-3-CARBOXYLATE | 409.2340 | |
| HA14-2 | 2-(2-AMINO-6-CHLORO-3-CYANO-4H-CHROMEN-4-YL)MALONONITRILE | 270.6780 | |
| HA14-3 | 2-(2-AMINO-6,8-DIBROMO-3-CYANO-4H-CHROMEN-4-YL)MALONONITRILE | 394.0250 | |
| HA14-4 | METHYL 2-AMINO-6-CHLORO-4-(1-CYANO-2-METHOXY-2-OXOETHYL)-4H-CHROMENE-3-CARBOXYLA | 336.7300 | |
| HA14-5 | 2-(2-AMINO-3-CYANO-6-METHOXY-4H-CHROMEN-4-YL)MALONONITRILE | 266.2590 | |

TABLE II-continued

Compounds for formula III

| Comp. Number | MOLNAME | M.W. | MOLSTRUCTURE |
| --- | --- | --- | --- |
| HA14-6 | ETHYL 2-AMINO-4-(1-CYANO-2-ETHOXY-2-OXOETHYL)-4H-CHROMENE-3-CARBOXYLATE | 330.3380 | 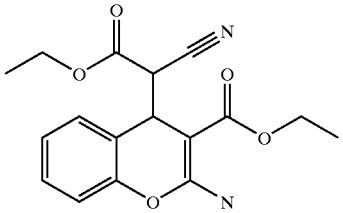 |
| HA14-7 | METHYL 2-AMINO-6,8-DIBROMO-4-(1-CYANO-2-METHOXY-2-OXOETHYL)-4H-CHROMENE-3-CARBOX | 460.0770 | 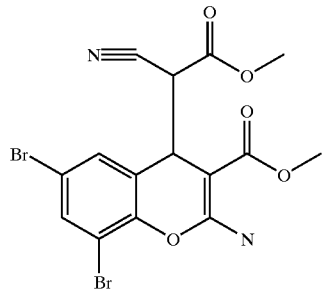 |
| HA14-8 | METHYL 2-AMINO-6-BROMO-4-(1-CYANO-2-METHOXY-2-OXOETHYL)-8-METHOXY-4H-CHROMENE-3- | 411.2070 | 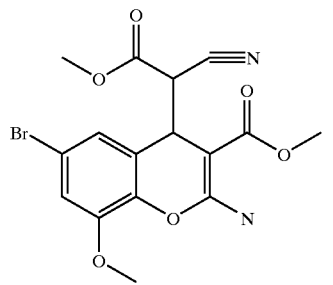 |
| HA14-9 | METHYL 2-AMINO-4-(DICYANOMETHYL)-4H-CHROMENE-3-CARBOXYLATE | 269.2590 | 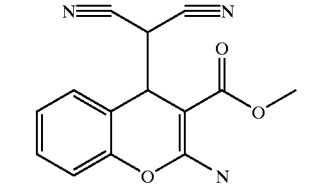 |
| HA14-10 | 2-(2-AMINO-6-BROMO-3-CYANO-4H-CHROMEN-4-YL)MALONONITRILE | 315.1290 | 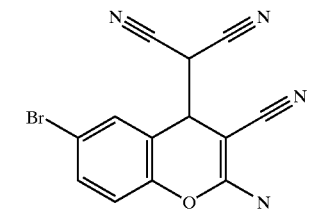 |
| HA14-11 | METHYL 2-AMINO-4-(1-CYANO-2-METHOXY-2-OXOETHYL)-4H-CHROMENE-3-CARBOXYLATE | 302.2850 | 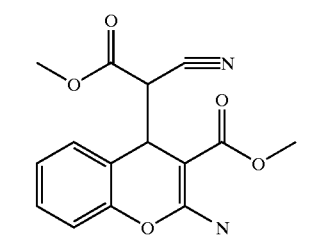 |

TABLE II-continued

Compounds for formula III

| Comp. Number | MOLNAME | M.W. | MOLSTRUCTURE |
|---|---|---|---|
| HA14-12 | ETHYL 2-AMINO-4-(DICYANOMETHYL)-4H-CHROMENE-3-CARBOXYLATE | 283.2860 | |
| HA14-13 | METHYL 2-AMINO-4-(1-CYANO-2-METHOXY-2-OXOETHYL)-6-NITRO-4H-CHROMENE-3-CARBOXYLAT | 347.2820 | |

The compounds of Table II are available from Maybridge Chemical Company. Particularly preferred compounds of formula III include compounds HA14-1 and HA14-8:

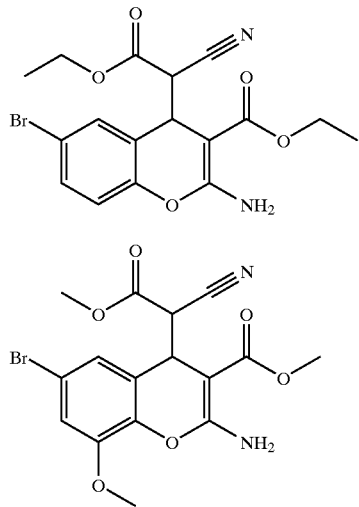

HA14-1

HA14-8

Bcl-2 Binding Assay for Candidate Inhibitors of Bcl-2

To measure the specific Bcl-2 binding of computer-predicted organic inhibitors, a Bcl-2 competition binding assay may be employed. The assay is based on fluorescence polarization. The assay can rapidly measure Bcl-2 receptor-ligand interaction without using filter binding, electrophoresis, or precipitation steps. Fluorescence polarization gives a direct, instantaneous equilibrium measure of the bound/free ratio between ligand and receptor molecules.

In order to set up the competition binding assay, the specific binding of a known peptide ligand of the targeted Bcl-2 functional pocket was first demonstrated. The peptide, designated peptide 1193 (GQVGRQLAIIGDDINR), is derived from the BH3 domain of the death agonist Bak. It has been shown in high-resolution X-ray structure to bind strongly to the Bcl-2 pocket (Muchmore et al., *Nature* 381:335–41, 1996; Saftler et al., *Science* 275:9836, 1997)

Peptide 1193 was synthesized and labeled with a fluorescein tracer (Flu-1193). The binding affinity of Flu-1193 to the Bcl-2 protein (purified soluble Bcl-2 proteins purchased from Santa Cruz Biotechnology, Inc., Calif.) was determined by a saturation experiment. Since the polarization value is derived from the ratio of bound versus free tracer, the lowest concentration of Flu-1193 was chosen, such that the concentration would yield a reasonable fluorescent signal and a stable polarization value. Using a fixed concentration of Flu-1193 peptide, Bcl-2 protein was titrated at increasing concentrations to achieve a saturated binding. The binding of the Flu-1193 peptide to Bcl-2 protein was measured on a LS-50 luminescence spectrometer equipped with polarizers using a dual path length quartz cell (500 $\mu$L) (Perkin-Elmer Corp.). The fluorophore is excited with vertical polarized light at 485 nm (excitation slit width 10 nm), and the polarization value of the emitted light is observed through vertical and horizontal polarizers at 520 nm (emission slit width 10 nm).

FIG. 1 illustrates a nonlinear least-squares fit for a saturation experiment using Flu-1193 and Bcl-2 protein in which the Bcl-2 concentration varied from 6 nM to 2 $\mu$M and Flu-1193 concentration remained at 30 nM. The dissociation constant $K_D$ of Flu-1193 was determined to be approximately 0.2 $\mu$M by using a nonlinear least-squares fit and single-site binding mode ($R^2=0.99$).

The binding affinity was also analyzed by Scatchard analysis. The Scatchard analysis is a standard method for analyzing the equilibrium binding parameters of a labeled molecule wily its target protein. The Scatchard plot is sensitive to presence of nonspecific binding, positive or negative cooperativity, and multiple classes of binding sites. The $K_D$ calculated from the Scatchard plot ($K_D=1$/slope), is approximately 0.25 $\mu$M which is in agreement with the value from dose-response calculation ($K_D\sim 0.20$ $\mu$M). The data fit best to linear function, indicating a single class of binding site.

Figure 2:
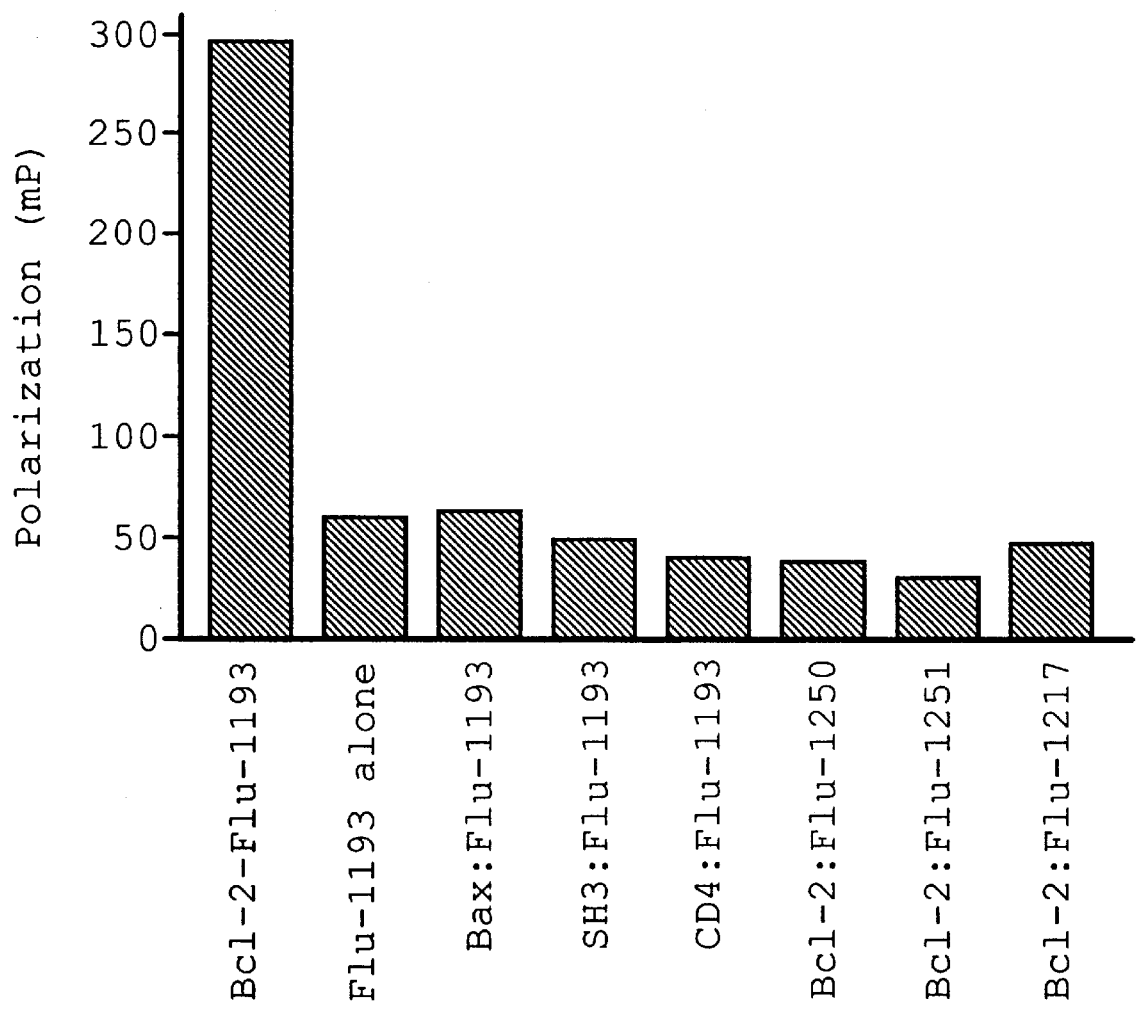
FIG. 2 is a graph of the binding interaction of fluorescein-labeled peptide 1193 (Flu-1193) with Bcl-2 protein (Bcl2:Flu-1193) and other proteins such as Bax, CD4, and the SH3 domain of the Bcr-Abl oncoprotein.

To further verify the specificity of the interaction of Flu-1193 and Bcl-2, a number of control experiments were carried out including measuring the binding of Flu-1193 to other proteins such as Bax, CD4, and the SH3 domain of the Bcr-Abl oncoprotein, and measuring the Bcl-2 binding of other Flu-labeled peptides derived from CD4 (Flu-1250 and Flu-1251) and Bcr-Abl SH3 (Flu-1217) (FIG. 2). The lack of binding interaction detected in these control systems (the signals were close to the background level of free Flu-1193), demonstrated the specificity of the binding of Flu-1193 to Bcl-2.

Using Flu-1193 as a specific probe, a competition binding protocol may be set up for non-peptide organic ligands of Bcl-2. The competition format utilizes fixed concentrations of Flu-1193 and Bcl-2 proteins (30 nM and 0.55 µM, respectively), with increasing concentrations of organic compounds added to generate inhibition curves. The binding equation proposed by Weinhold et al., *J Am. Chem. Soc.* 114:9270–9275, 1992, is then used to derive the dissociation constant $K_D$ of an inhibitor from its competition inhibition curve, $$[Inhibitor] = \frac{K_D}{K_L}\left[[Bcl-2]\times\left(\frac{A_B-A}{A-A_F}\right)-[Flu-1193]\times\left(\frac{A_B-A}{A_B-A_F}\right)\right]-K_D$$

wherein [Inhibitor], [Bcl-2], and [Flu-1193] are the concentrations of inhibitor, Bcl-2 protein and Flu-1193 peptide, respectively; $K_L$ is the dissociation constant of the Flu-1193 peptide; A is the observed fluorescence anisotropy, A=2P/(3-P), where P is the observed fluorescence polarization values; and $A_B$ and $A_F$ are fluorescence anisotropy values when all of the Flu-1193 peptide is either bound to the Bcl-2 protein ($A_B$) or free in solution ($A_F$). The $K_D$ value is adjusted by a factor of 5 as suggested by others for FP-based assays.

The dissociation constant of small molecule organic inhibitors of Bcl-2 identified in the foregoing binding assay with peptide Flu-1193 is preferably no more than about 500 µM, preferably no more than about 100 µM, most preferably no more than about 10 µM.

Biological Activity Assay of Candidate Inhibitors of Bcl-2

The small organic compounds which bind to the active pocket of Bcl-2 as described above may be tested for inhibition of Bcl-2 biological activity, and hence the ability to induce apoptosis in cancer cells where Bcl-2 proteins play a role in resisting apoptosis.

DNA fragmentation is an important and characteristic marker of apoptosis. Accordingly, cells of a variant of HL-60 are incubated with test compound at 100 µM concentration for 24 hours. The DNA of the cells is then isolated by conventional techniques and analyzed for fragmentation on 2% agarose gels containing 0.2 µg/ml ethidium bromide. Visible DNA fragmentation resulting from incubation of 100 µM of compound with the cells for 24 hours generally indicates that the compound is active in inducing apoptosis.

Therapeutic Administration

The small molecule inhibitors of Bcl-2 function may be used to treat any condition characterized by the accumulation of cells which are regulated by Bcl-2. For the most part, the cells express or overexpress Bcl-2. Enhancement of Bcl-2 expression has been demonstrated to increase the resistance of cells to almost any apoptotic signal (Hockenbery et al., *Nature* 348, 334 (1990); Nuñez et al., *Immunol.* 144, 3602 (1990); Vaux et al., *Nature* 335,440 (1988); Hockenbery et al., *Cell* 75, 241 (1993); Ohmori et al., *Res. Commun.* 192, 30 (1993); Lotem et al., *Cell Growth. Differ* 4, 41 (1993); Miyashita et al., *Blood* 81, 115 (1993); Minn et al.)). Principally, the proliferative disorders associated with the inhibition of cell apoptosis include cancer, autoimmune disorders and viral infections. Overexpression of Bcl-2 specifically prevents cells from initiating apoptosis in response to a number of stimuli (Hockenbery et al., *Nature* 348, 334 (1990); Nunez et al., *J Immunol.* 144, 3602 (1990); Vaux et al., *Nature* 335, 440 (1988); Hockenbery et al., *Cell* 75, 241 (1993)). The induction of genes that inhibit Bcl-2 can induce apoptosis in a wide variety of tumor types, suggesting that many tumors continually rely on Bcl-2 or related gene products to prevent cell death. Bcl-2 expression has been associated with a poor prognosis in at least prostatic cancer, colon cancer and neuroblastoma (McDonnell et al., *Cancer Res.* 52, 6940 (1992); Hague et al., *Oncogene* 9, 3367 (1994); Castle et al., *Am. J. Pathol.* 143, 1543 (1993)). Bcl-2 or the related gene $Bcl_x$ has been found to confer resistance to cell death in response to several chemotherapeutic agents (Ohmori et al., *Res. Commun.* 192, 30 (1993); Lotem et al., *Cell Growth.Differ*4, 41 (1993); Miyashita et al., *Blood* 81, 115 (1993); Minn et al.)).

Physiologic cell death is important for the removal of potentially autoreactive lymphocytes during development and for the removal of excess cells after the completion of an immune response. Failure to remove these cells can result in autoimmune disease. A lupus-like autoimmune disease has been reported in transgenic mice constitutively overexpressing Bcl-2 in their B cells (Stressed et al., *Proc. Natl. Acad. Sci. USA* 88, 8661 (1991)). Linkage analysis has established an association between the Bcl-2 locus and autoimmune diabetes in non-obese diabetic mice (Garchon et al., *Eur. J. Immunol.* 24, 380 (1994). The compounds of the invention may be used to induce apoptosis of self-reactive lymphocytes. By "self-reactive" is meant a lymphocyte which participates in an immune response against antigens of host cells or host tissues.

The small molecule inhibitors of Bcl-2 function may be used in the treatment of viral infection, to induce apoptosis of virally infected cells. Viruses have developed mechanisms to circumvent the normal regulation of apoptosis in virus-infected cells, and theses mechanisms have implicated Bcl-2. For example, the E1B 19-kDa protein is instrumental in the establishment of effective adenoviral infection. The apoptosis-blocking ability of E1B can be replaced in adenoviruses by Bcl-2 (Boyd et al., *Cell*79, 341 (1994)). Genes of certain other viruses have been shown to have sequence and functional homology to Bcl-2 (Neilan et al., *J. Virol.* 67, 4391 (1993); Henderson et al., *Proc. Natl. Acad. Sci. U.S.A.* 90, 8479 (1993)). The viral gene LMP-1 specifically upregulates Bcl-2 providing a survival advantage over latently infected cells (Henderson et al., *Cell* 65, 1107 (1991)). Sindbis infection is dependent on the host cell's expression of Bcl-2 (Levine et al., *Nature* 361,739 (1993)).

The effective amount of compound needed to treat a subject may be routinely determined through procedures well known to those skilled in the art which address such parameters as biological half-life, bioavailability, and toxicity. Such determination is well within the capability of those skilled in the art, especially in light of the detailed disclosure provided herein.

The present invention provides pharmaceutical compositions that comprise the compounds of the invention and pharmaceutically acceptable carriers or diluents.

For parenteral administration, the compounds of the invention can be, for example, formulated as a solution, suspension, or lyophilized powder in association with a pharmaceutically acceptable parenteral vehicle. Examples of such vehicles are water, saline, Ringer's solution, dextrose solution, and 5% human serum albumin. The vehicle or lyophilized powder may contain additives that maintain isotonicity (e.g., sodium chloride, mannitol) and chemical stability (e.g., buffers and preservatives). For example, a parenteral composition suitable for administration by injection is prepared by dissolving 1.5% by weight of active ingredient in 0.9% sodium chloride solution. The formulation can be sterilized by any commonly used technique.

The pharmaceutical compositions according to the invention may be administered as a single dose or in multiple doses. The pharmaceutical compositions of the present invention may be administered either as individual therapeutic agents or in combination with each other or with other therapeutic agents. The treatments of the present invention may be combined with conventional therapies, which may be administered sequentially or simultaneously.

The pharmaceutical compositions of the present invention may be administered by any means that enables the active agent to reach the targeted cells. Because compounds of the invention may be subject to being digested when administered orally, parenteral administration, i.e., intravenous, subcutaneous or intramuscular, would ordinarily be used to optimize absorption. Intravenous administration may be accomplished with the aid of an infusion pump. Alternatively, the compounds of the invention can be formulated as aerosol medicaments for intranasal inhalation or topical administration.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of the compound of the invention can be about 1 to 3000 milligrams per 50 kilograms of body weight; preferably 10 to 1000 milligrams per 50 kilograms of body weight; more preferably 25 to 80 milligrams per 50 kilograms of body weight. Ordinarily, 8 to 800 milligrams are administered to an individual per day in divided doses 1 to 6 times a day or in sustained release form is effective to obtain desired results.

EXAMPLE 1

Bcl-2 Ligand Binding Assay

The binding of selected organic compounds to Bcl-2 protein in the presence of peptide Flu-1193 was measured on a LS-50 luminescence spectrometer equipped with polarizers using a dual path length quartz cell (500 µL) (Perkin-Elmer Corp.). The fluorophore was excited with vertical polarized light at 485 nm (excitation slit width 10 nm). The polarization value of the emitted light was observed through vertical and horizontal polarizers at 520 nm (emission slit width 10 nm). Fixed concentrations of Flu-1193 and Bcl-2 proteins (30 nM and 0.55 µM, respectively), with increasing concentrations of test compound was added to generate inhibition curves. The binding equation proposed by Weinhold et al., *J. Am. Chem. Soc.* 114:9270–9275, 1992, was used to derive the dissociation constant $K_D$ of the test compound from its competition inhibition curve, $$[Inhibitor] = \frac{K_D}{K_L}\left[[Bcl-2] \times \left(\frac{A_B - A}{A - A_F}\right) - [Flu-1193] \times \left(\frac{A_B - A}{A_B - A_F}\right)\right] - K_D$$

wherein [Inhibitor], [Bcl-2], and [Flu-1193] are the concentrations of inhibitor, Bcl-2 protein and Flu-1193 peptide, respectively; $K_L$ is the dissociation constant of the Flu-1193 peptide; A is the observed fluorescence anisotropy, A=2P/(3-P), where P is the observed fluorescence polarization values; and $A_B$ and $A_F$ are fluorescence anisotropy values when all of the Flu-1193 peptide is either bound to the Bcl-2 protein ($A_B$) or free in solution ($A_F$).

According to this binding protocol, 716 organic compounds selected from computer screening studies were initially tested at 100 µM concentration. A group of compounds found to be active in the assay with a level of inhibition ranging from 35% to 98%. Four of the active compounds comprised compounds HA12-16 (compound HA12-16 may also be identified herein as "HA01"), HA02, HA03 and HA04. A clear concentration-dependent competition binding was observed for these compounds and their biding affinities determined by the above procedure. The two most potent compounds, HA12-16 and HA02, exhibited a binding affinity ($K_D$) of 7 µM and 15 µM, respectively.

Figure 6:
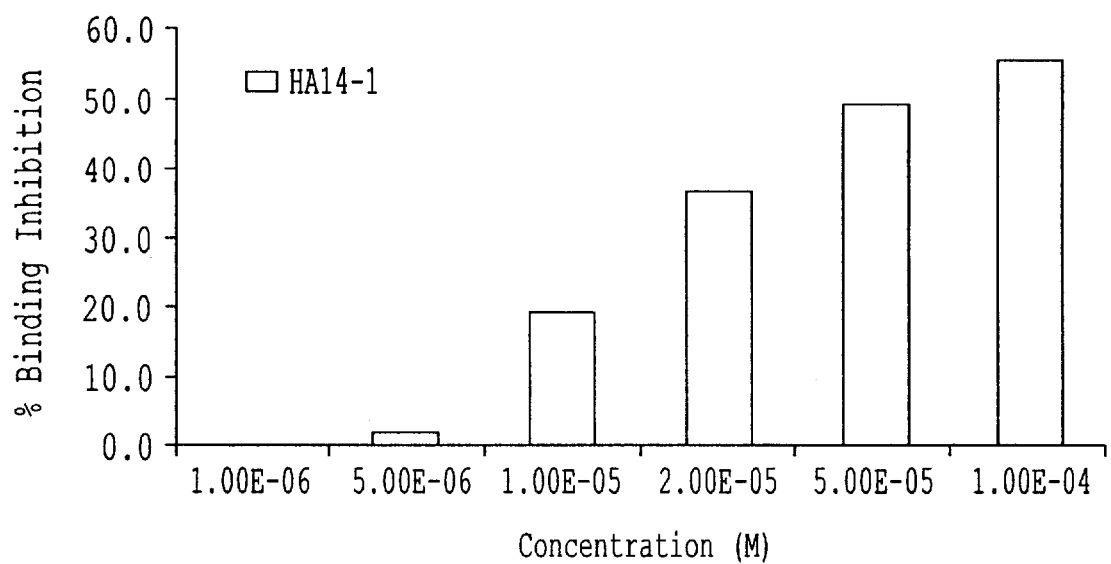
FIG. 6 is a graph of an assay measuring the binding of compound HA14-1 to Bcl-2 protein.

Compound HA14-1 was tested in the same manner. A clear concentration-dependent competition binding was observed for this compound over a concentration of from 1 to 100 µM. The results are set forth in FIG. 6.

EXAMPLE 2

DNA Fragmentation Assay A

The cells for this assay comprised a variant of the human myeloid leukemia HL-60 cell line transfected with Bcl-2 to overexpress Bcl-2 (Liu et al., *Cell* 86:147–57, 1996). Cells of the parent line are sensitive to 50 µM of the apoptosis-inducing drug etoposide. The Bcl-2-transfected line is resistant to the same concentration of drug, indicating that Bcl-2 blocked apoptosis by the drug.

The Bcl-transfected cells were incubated with Bcl-2 inhibitor test compounds at 50 µM for 24 hours and then examined for apoptosis by the following DNA fragmentation assay. Then the treated cells were washed in PBS, lysed in digestion buffer (100 mM NaCl, 10 mM Tris-Cl, pH8, 25 mM EDTA, pH 8, 0.5% SDS, 0.1 mg/ml proteinase K), and incubated overnight at 50° C. The samples were extracted three times with phenol-chloroform, precipitated with an equal volume isopropanol, and spun down for 15 minutes in a microcentrifuge at room temperature. The DNA precipitate was washed once with 70% ethanol and resuspended in TE buffer containing 200 µg/ml DNase-free RNase A (Boehringer Mannheim, Indianapolis, Ind.). Alter incubation at 37° C. for 30 min., the DNA was loaded into a 2% agarose mini-gel with 2 µg/ml ethidium bromide, and electrophoresis is run at 50 V for 2 hours in 0.5×TBE buffer. The gel was destained with water for 1 hour arid photographed under UV light.

Figure 3:
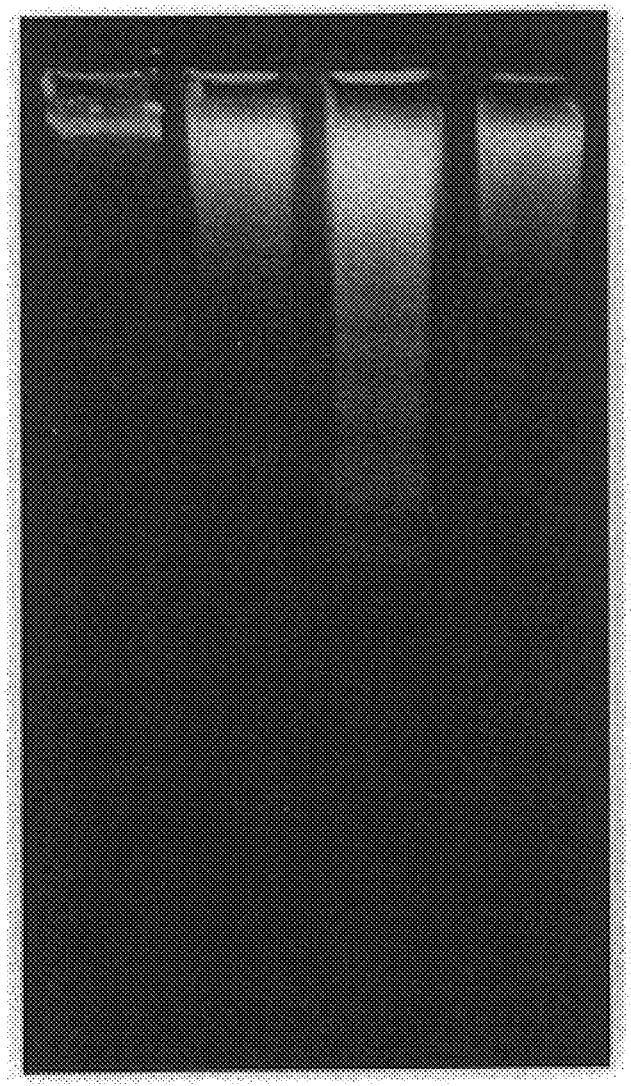
FIG. 3 is a DNA fragmentation assay of HL-60 cells transfected to overexpress Bcl-2 and treated with compound HA13, HA14 or HA11-57: lane 0, control; lane 1, HA13; lane 2, HA14; lane 3, HA11-57.

The results are shown in FIG. 3: lane 0, control; lane 1, compound HA13; lane 2, compound HA14; lane 3, compound HA11-57. DNA fragmentation is apparent in each lane, except for the control, indicating that each compound is effective in reversing Bcl-2 block of apoptosis.

EXAMPLE 3

DNA Fragmentation Assay B

Figure 4:
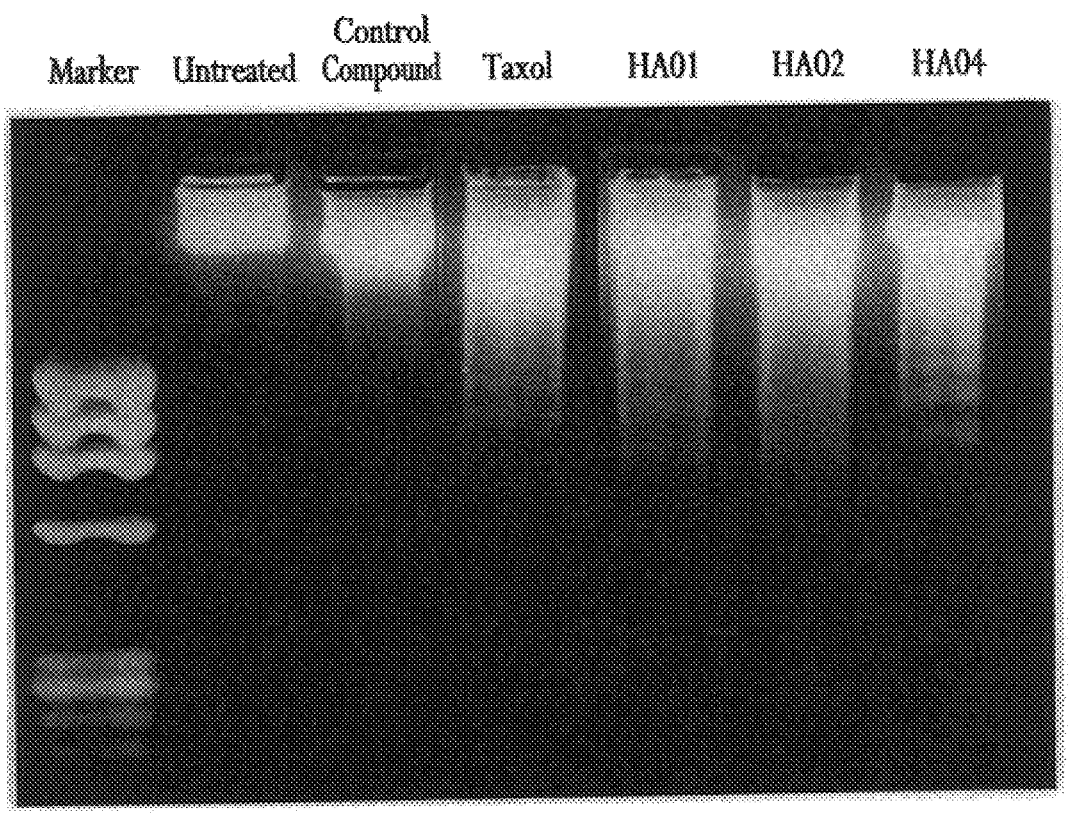
FIG. 4 is a DNA fragmentation assay of 697 cells treated with compound HA01, HA02 HA04, Taxol or negative control compound having no affinity for Bcl-2.

The assay of Example 2 was repeated for compounds HA01 (also designated "HA12-16"), HA02 and HA04, with the following modifications. First, the ethidium bromide stain concentration was 1 µg/ml instead of 2 µg/ml. Second, the cells for the assay comprised 697 cells. The 697 line is a human pre-B leukemia line with a t(1; 19) chromosomal translocation (no translocation involving Bcl-2). Bcl-2 is highly expressed in this line. The high expression of Bcl-2 in 697 cells was confirmed by protein immunoblot analysis (data not shown). Taxol (Sigma Chemical Co., St. Louis, Mo.), a widely-used anticancer drug known to induce apoptosis in 697 cells, was used as a positive control. A randomly selected organic compound which was inactive in the Bcl-2 binding assay was included in the assay as a negative control. DNA markers were phiX174 DNA with restriction endonuclease Hae III (Boehringer Mannheim, Indianapolis, Ind.). The cells were incubated with test compound at 50 μM concentration or Taxol at 5 μM concentration for 48 hours. The results are shown in FIG. 4. The test compounds induced DNA fragmentation to various extents while the control compound did not show any effect.

A control experiment was carried out to investigate the specificity of the apoptosis-inducing effect of the compounds in a human myeloid leukemia HL-60 neo line in which apoptosis is not regulated by Bcl-2. the lack of effect in inducing apoptosis of the HL-60 neo cells by a representative compound HA01 at the same concentration (50 μM) which induced apoptosis in the 697 cells (data not shown) indicated the specificity of the compound for the Bcl-2 mediated apoptotic pathway.

EXAMPLE 4

DNA Fragmentation Assay C

Figure 5:
FIG. 5 is a DNA fragmentation assay of HL-60 cells transfected to overexpress Bcl-2 and treated with compound HA14-1. Lane A: cells treated with HA14-1; lane B, cells pretreated with fluoromethyl ketone, then treated with HA14-1.

The assay of Example was repeated by incubating HL-60 Bcl-2 cells with compound HA14-1 (50 μM for 24 hours). Alternatively, the cells were first pretreated with 100 μM fluoromethyl ketone at 100 μM for 2 hours, followed by 50 μM HA14-1 for 24 hours. The results are set forth in FIG. 5: lane A, HA14-1; lane B, fluoromethyl ketone and HA14-1. Fluoromethyl ketone is an inhibitor of a downstream target of Bcl-2. Fluoromethyl ketone pretreatment of HL-60 Bcl-2 cells should neutralize the action of HA14-1. This is indeed shown in FIG. 5, lane B.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A method of inducing apoptosis of cells in a subject, which said cells are regulated by Bcl-2, comprising administering to the subject an effective amount of an active compound of the formula III:

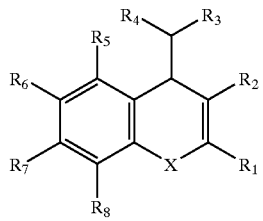

III wherein:
X is selected from the group consisting of $CH_2$; $CHOCH_3$; NH; $NCH_3$; O; and S;
$R_1$ is selected from the group consisting of OH; $NH_2$; CHO; $COCH_3$; COOH; $N(C_{1-3}$ alkyl$)_2$; $NH(C_{1-3}$ alkyl); $OCOCH_3$; $OCOCH_2CH_3$; $NHCOCH_3$; $NHNHCOCH_3$; $NHNHCONH_2$; $N(C_{1-3}$ alkyl$)_2$; $NH(C_{1-3}$ alkyl);
$R_2$ is selected from the group consisting of $C_{1-3}$ alkyl; $C_{1-3}$ alkoxy; OH; $NH_2$; CHO; $COCH_3$; $OCOCH_3$; $OCOCH_2CH_3$; COOH; $COOCH_3$;$COOCH_2CH_3$; $COOCH_2CH_2CH_3$;

$R_3$ is selected from the group consisting of $C_{1-3}$ alkyl; $C_{1-3}$ alkoxy; CN; $CH_2CN$; $CH_2NO_2$; CHO; $COCH_3$; COOH; $OCOCH_3$; $OCOCH_2CH_3$; $NHCOCH_3$; $NHNHCOCH_3$; $NHNHCONH_2$; $CH=CH_2$; $CH_2CH=CH_2$; $CH_2CHO$;

$R_4$ is selected from the group consisting of $C_{1-3}$ alkyl; $C_{1-3}$ alkoxy; CN; $CH_2CN$; $CH_2NO_2$; CHO; $COCH_3$; $COCH_3$; COOH; $COOCH_3$; $COOCH_2CH_3$; $COOCH_2CH_2CH_3$; $OCOCH_3$; $OCOCH_2CH_3$;

$R_5$ is selected from the group consisting of hydrogen $CH_3$; $OCH_3$; OH: $NH_2$; Br; Cl; and F; and $R_6$, $R_7$ and $R_8$ are selected from the group consisting of hydrogen, $CH_3$; $CH_2CH_3$; $CF_3$; $NH_2$; OH; $OCH_3$; CN; $NO_2$; Cl; Br; F; COOH; and $COOCH_3$; provided, at least one member of the group $R_6$, $R_7$ or $R_8$ must be Cl, Br or F when the remaining members of said group are hydrogen;

or a pharmaceutically acceptable salt thereof when the compound includes at least one $NH_2$ or COOH substituent.

2. The method according to claim 1 wherein the compound has a dissociation constant of not more than about 500 μM for binding the hydrophobic pocket on the Bcl-2 protein formed by the BH1, BH2, and BH3 domains of the Bcl-2 protein.

3. The method according to claim 1 wherein $R_1$ and $R_3$ are selected from the group consisting of piperidinyl, piperazinyl, morpholino, pyrimidyl, pyrrolyl, pyrrolidino and imidazyl.

4. The method according to claim 1 wherein $R_2$ and $R_4$ are selected from the group consisting of $COCH_3$; $OCOCH_3$; $OCOCH_2CH_3$; COOH; $COOCH_3$; $COOCH_2CH_3$; and $COOCH_2CH_2CH_3$.

5. The method according to claim 1 wherein:
$R_5$ is selected from the group consisting of hydrogen, Br; Cl; and F;
$R_6$, $R_7$ $R_8$ are independently selected from the group consisting of $NH_2$; OH; $OCH_3$; CN; $NO_2$; Cl; Br; F.

6. The method according to claim 1 wherein the compound is selected from the group consisting of HA14-1 and HA14-8:

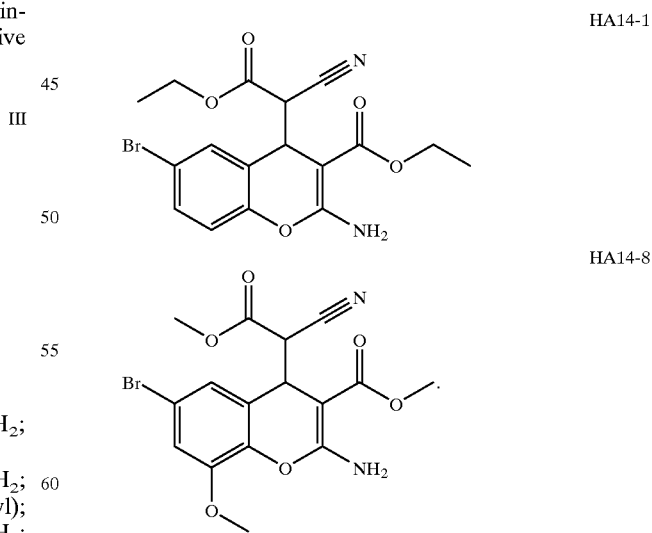

7. The method according to claim 1 wherein the compound causes the fragmentation of DNA in a Bcl-2 transfected HL-60 cell line when incubated with such cells at a concentration of not more than 100 μM for 24 hours.

8. The method according to claim 1 wherein the cells induced to undergo apoptosis comprise cancer cells.

9. The method according to claim 1 wherein the cells induced to undergo apoptosis comprise virus-infected cells.

10. The method according to claim 1 wherein the cells induced to undergo apoptosis comprise self-reactive lymphocytes.

11. A method of reversing Bcl-2-mediated blockage of apoptosis in cancer cells comprising contacting said cells with a compound of the formula III:

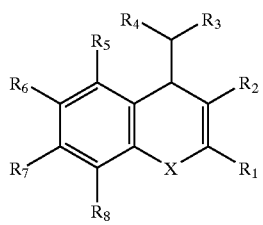

III wherein:
- X is selected from the group consisting of $CH_2$; $CHOCH_3$; NH; $NCH_3$; O; and S;
- $R_1$ is selected from the group consisting of OH; $NH_2$; CHO; $COCH_3$; COOH; $N(C_{1-3}\ alkyl)_2$; $NH(C_{1-3}\ alkyl)$; $OCOCH_3$; $OCOCH_2CH_3$; $NHCOCH_3$; $NHNHCOCH_3$; $NHNHCONH_2$; $N(C_{1-3}\ alkyl)_2$; $NH(C_{1-3}\ alkyl)$; and five- and six-member heterocyclic rings;
- $R_2$ is selected from the group consisting of $C_3$ alkyl; $C_{1-3}$ alkoxy; OH; $NH_2$; CHO; $COCH_3$; $OCOCH_3$; $OCOCH_2CH_3$; COOH; $COOCH_3$; $COOCH_2CH_3$; $COOCH_2CH_2CH_3$;
- $R_3$ is selected from the group consisting of $C_{1-3}$ alkyl; $C_{1-3}$ alkoxy; CN; $CH_2CN$; $CH_2NO_2$; CHO; $COCH_3$; COOH; $OCOCH_3$; $OCOCH_2CH_3$; $NHCOCH_3$; $NHNHCOCH_3$; $NHNHCONH_2$; $CH=CH_2$; $CH_2CH=CH_2$; $CH_2CHO$; and five- and six-member heterocyclic rings;
- $R_4$ is selected from the group consisting of $C_3$ alkyl; $C_{1-3}$ alkoxy; CN; $CH_2CN$; $CH_2NO_2$; CHO; $COCH_3$; $COCH_3$; COOH; $COOCH_3$; $COOCH_2CH_3$; $COOCH_2CH_2CH_3$; $OCOCH_3$; $OCOCH_2CH_3$;
- $R_5$ is selected from the group consisting of hydrogen $CH_3$; $OCH_3$; OH: $NH_2$; Br; Cl; and F; and
- $R_6$, $R_7$ and $R_8$ are selected from the group consisting of hydrogen, $CH_3$; $CH_2CH_3$; $CF_3$; $NH_2$; OH; $OCH_3$; CN; $NO_2$; Cl; Br; F; COOH; and $COOCH_3$; provided, at least one member of the group $R_6$, $R_7$ or $R_8$ must be Cl, Br or F when the remaining members of said group are hydrogen;

or a pharmaceutically acceptable salt thereof when the compound includes at least one $NH_2$ or COOH substituent.

12. A method for treating a subject afflicted with a cancer characterized by cancer cells which express Bcl-2 comprising administering to the subject an effective amount of a compound of the formula III:

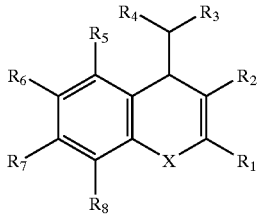

III wherein:
- X is selected from the group consisting of $CH_2$; $CHOCH_3$; NH; $NCH_3$; O; and S;
- $R_1$ is selected from the group consisting of OH; $NH_2$; CHO; $COCH_3$; COOH; $N(C_{1-3}\ alkyl)_2$; $NH(C_{1-3}\ alkyl)$; $OCOCH_3$; $OCOCH_2CH_3$; $NHCOCH_3$; $NHNHCOCH_3$; $NHNHCONH_2$; $N(C_{1-3}\ alkyl)_2$; $NH(C_{1-3}\ alkyl)$; and five- and six-member heterocyclic rings;
- $R_2$ is selected from the group consisting of $C_{1-3}$ alkyl; $C_{1-3}$ alkoxy; OH; $NH_2$; CHO; $COCH_3$; $OCOCH_3$; $OCOCH_2CH_3$; COOH; $COOCH_3$; $COOCH_2CH_3$; $COOCH_2CH_2CH_3$;
- $R_3$ is selected from the group consisting of $C_{1-3}$ alkyl; $C_{1-3}$ alkoxy; CN; $CH_2CN$; $CH_2NO_2$; CHO; $COCH_3$; COOH; $OCOCH_3$; $OCOCH_2CH_3$; $NHCOCH_3$; $NHNHCOCH_3$; $NHNHCONH_2$; $CH=CH_2$; $CH_2CH=CH_2$; $CH_2CHO$; and five- and six-member heterocyclic rings;
- $R_4$ is selected from the group consisting of $C_{1-3}$ alkyl; $C_{1-3}$ alkoxy; CN; $CH_2CN$; $CH_2NO_2$; CHO; $COCH_3$; $COCH_3$; COOH; $COOCH_3$; $COOCH_2CH_3$; $COOCH_2CH_2CH_3$; $OCOCH_3$; $OCOCH_2CH_3$;
- $R_5$ is selected from the group consisting of hydrogen $CH_3$; $OCH_3$; OH: $NH_2$; Br; Cl; and F; and
- $R_6$, $R_7$ and $R_8$ are selected from the group consisting of hydrogen, $CH_3$; $CH_2CH_3$; $CF_3$; $NH_2$; OH; $OCH_3$; CN; $NO_2$; Cl; Br; F; COOH; and $COOCH_3$; provided, at least one member of the group $R_6$, $R_7$ or $R_8$ must be Cl, Br or F when the remaining members of said group are hydrogen;

or a pharmaceutically acceptable salt thereof when the compound includes at least one $NH_2$ or COOH substituent.

13. A method according to claim 12 wherein the cancer is selected from the group of cancers consisting of prostate, colorectal, gastric, non-small lung, renal and thyroid cancers, neuroblastoma, melanoma, and acute and chronic lymphocytic and non-lymphocytic leukemia.

* * * * *